US009080209B2

(12) United States Patent
Sappenfield

(10) Patent No.: US 9,080,209 B2
(45) Date of Patent: Jul. 14, 2015

(54) NON-MASS DETERMINED BASE COMPOSITIONS FOR NUCLEIC ACID DETECTION

(75) Inventor: Christopher C. Sappenfield, San Diego, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 13/389,139

(22) PCT Filed: Aug. 6, 2010

(86) PCT No.: PCT/US2010/044774
§ 371 (c)(1),
(2), (4) Date: Apr. 4, 2012

(87) PCT Pub. No.: WO2011/017656
PCT Pub. Date: Feb. 10, 2011

(65) Prior Publication Data
US 2012/0183970 A1    Jul. 19, 2012

Related U.S. Application Data

(60) Provisional application No. 61/231,907, filed on Aug. 6, 2009.

(51) Int. Cl.
*C12Q 1/68* (2006.01)
(52) U.S. Cl.
CPC .................................... *C12Q 1/6869* (2013.01)
(58) Field of Classification Search
None
See application file for complete search history.

(56) References Cited

U.S. PATENT DOCUMENTS

| | | |
|---|---|---|
| 5,436,129 A | 7/1995 | Stapleton |
| 5,451,500 A | 9/1995 | Stapleton |
| 5,484,908 A | 1/1996 | Froehler et al. |
| 5,523,217 A | 6/1996 | Lupski et al. |
| 5,547,835 A | 8/1996 | Koster |
| 5,567,587 A | 10/1996 | Kohne |
| 5,605,798 A | 2/1997 | Koster |
| 5,622,824 A | 4/1997 | Koster |
| 5,683,869 A | 11/1997 | Ramsay Shaw et al. |
| 5,691,141 A | 11/1997 | Koster |
| 5,707,802 A | 1/1998 | Sandhu et al. |
| 5,727,202 A | 3/1998 | Kucala |
| 5,745,751 A | 4/1998 | Nelson et al. |
| 5,759,771 A | 6/1998 | Tilanus |
| 5,763,169 A | 6/1998 | Sandhu et al. |
| 5,777,324 A | 7/1998 | Hillenkamp |
| 5,832,489 A | 11/1998 | Kucala |
| 5,849,492 A | 12/1998 | Rogan |
| 5,849,901 A | 12/1998 | Mabilat et al. |
| 5,851,765 A | 12/1998 | Koster |
| 5,871,697 A | 2/1999 | Rothberg et al. |
| 5,872,003 A | 2/1999 | Koster |
| 5,900,481 A | 5/1999 | Lough et al. |
| 5,928,906 A | 7/1999 | Koster et al. |
| 5,965,363 A | 10/1999 | Monforte et al. |
| 5,972,693 A | 10/1999 | Rothberg et al. |
| 5,976,798 A | 11/1999 | Parker et al. |
| 5,981,176 A | 11/1999 | Wallace |
| 5,981,190 A | 11/1999 | Israel |
| 6,001,564 A | 12/1999 | Bergeron et al. |
| 6,018,713 A | 1/2000 | Coli et al. |
| 6,024,925 A | 2/2000 | Little et al. |
| 6,043,031 A | 3/2000 | Koster et al. |
| 6,051,378 A | 4/2000 | Monforte et al. |
| 6,055,487 A | 4/2000 | Margery et al. |
| 6,060,246 A | 5/2000 | Summerton et al. |
| 6,061,686 A | 5/2000 | Gauvin et al. |
| 6,074,823 A | 6/2000 | Koster |
| 6,074,831 A | 6/2000 | Yakhini et al. |
| 6,090,558 A | 7/2000 | Butler et al. |
| 6,111,251 A | 8/2000 | Hillenkamp |
| 6,133,436 A | 10/2000 | Koster et al. |
| 6,140,053 A | 10/2000 | Koster |
| 6,146,854 A | 11/2000 | Koster et al. |
| 6,180,339 B1 | 1/2001 | Sandhu et al. |
| 6,180,372 B1 | 1/2001 | Franzen |
| 6,194,144 B1 | 2/2001 | Koster |

(Continued)

FOREIGN PATENT DOCUMENTS

| DE | 19802905 A1 | 7/1999 |
|---|---|---|
| DE | 19824280 A1 | 12/1999 |

(Continued)

OTHER PUBLICATIONS

Gupta et al. (Single-molecule DNA sequencing technologies for future genomics research, Trends Biotechnol. Nov. 2008;26(11):602-11, Epub Aug. 21, 2008).*
Ju et al. (Four-color DNA sequencing by synthesis using cleavable fluorescent nucleotide reversible terminators, PNAS, vol. 103, No. 52, pp. 19635-19640, Dec. 26, 2006).*
Korlach et al. (Selective aluminum passivation for targeted immobilization of single DNA polymerase molecules in zero-mode waveguide nanostructures, PNAS, vol. 105, No. 4, Jan. 29, 2008).*
Shendure et al. (Next-generation DNA sequencing, Nature Biotechnology, vol. 26, No. 10, Oct. 9, 2008.*

(Continued)

*Primary Examiner* — Christopher M Babic
*Assistant Examiner* — Aaron Priest
(74) *Attorney, Agent, or Firm* — David A. Casimir; Casimir Jones, S.C.

(57) ABSTRACT

The present invention provides systems, methods, and compositions for nucleic acid detection based on non-mass determined base compositions. For example, in certain embodiments, base count data for a template nucleic acid is generated using an approach that does not measure molecular mass of the template nucleic acid (e.g., by sequencing the template nucleic acid) and a database comprising base count entries is queried to identify the target nucleic acid. In particular embodiments, sequencing is employed which is conducted in substantially real-time.

29 Claims, 6 Drawing Sheets

(56) References Cited

U.S. PATENT DOCUMENTS

| | | |
|---|---|---|
| 6,197,498 B1 | 3/2001 | Koster |
| 6,221,598 B1 | 4/2001 | Schumm et al. |
| 6,221,601 B1 | 4/2001 | Koster et al. |
| 6,221,605 B1 | 4/2001 | Koster |
| 6,225,450 B1 | 5/2001 | Koster |
| 6,235,478 B1 | 5/2001 | Koster |
| 6,238,871 B1 | 5/2001 | Koster |
| 6,258,538 B1 | 7/2001 | Koster et al. |
| 6,268,131 B1 | 7/2001 | Kang et al. |
| 6,268,144 B1 | 7/2001 | Koster |
| 6,277,573 B1 | 8/2001 | Koster |
| 6,300,076 B1 | 10/2001 | Koster |
| 6,303,297 B1 | 10/2001 | Lincoln et al. |
| 6,322,970 B1 | 11/2001 | Little et al. |
| 6,389,428 B1 | 5/2002 | Rigault et al. |
| 6,393,367 B1 | 5/2002 | Tang et al. |
| 6,419,932 B1 | 7/2002 | Dale |
| 6,423,966 B2 | 7/2002 | Hillenkamp et al. |
| 6,428,955 B1 | 8/2002 | Koster et al. |
| 6,436,635 B1 | 8/2002 | Fu et al. |
| 6,453,244 B1 | 9/2002 | Oefner |
| 6,468,743 B1 | 10/2002 | Romick et al. |
| 6,468,748 B1 | 10/2002 | Monforte et al. |
| 6,475,143 B2 | 11/2002 | Iliff |
| 6,500,621 B2 | 12/2002 | Koster |
| 6,553,317 B1 | 4/2003 | Lincoln et al. |
| 6,558,902 B1 | 5/2003 | Hillenkamp |
| 6,566,055 B1 | 5/2003 | Monforte et al. |
| 6,589,485 B2 | 7/2003 | Koster |
| 6,602,662 B1 | 8/2003 | Koster et al. |
| 6,605,433 B1 | 8/2003 | Fliss et al. |
| 6,613,520 B2 | 9/2003 | Ashby |
| 6,680,476 B1 | 1/2004 | Hidalgo et al. |
| 6,706,530 B2 | 3/2004 | Hillenkamp |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,419,787 B2 | 9/2008 | Köster |
| 7,501,251 B2 | 3/2009 | Köster et al. |
| 7,741,036 B2 | 6/2010 | Ecker et al. |
| 2002/0042112 A1 | 4/2002 | Koster et al. |
| 2002/0055101 A1 | 5/2002 | Bergeron et al. |
| 2002/0138210 A1 | 9/2002 | Wilkes et al. |
| 2002/0168630 A1 | 11/2002 | Fleming et al. |
| 2003/0027135 A1 | 2/2003 | Ecker et al. |
| 2003/0113745 A1 | 6/2003 | Monforte et al. |
| 2003/0129589 A1 | 7/2003 | Koster et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0190605 A1 | 10/2003 | Ecker et al. |
| 2003/0228597 A1 | 12/2003 | Cowsert et al. |
| 2004/0023209 A1* | 2/2004 | Jonasson .................. 435/5 |
| 2004/0081993 A1 | 4/2004 | Cantor et al. |
| 2004/0110169 A1 | 6/2004 | Ecker et al. |
| 2004/0202997 A1 | 10/2004 | Ecker et al. |
| 2006/0062531 A1* | 3/2006 | Turner et al. .............. 385/123 |
| 2007/0099212 A1* | 5/2007 | Harris ........................ 435/6 |
| 2007/0218489 A1* | 9/2007 | Sampath et al. ............. 435/6 |
| 2008/0108082 A1* | 5/2008 | Rank et al. ................. 435/6 |
| 2008/0146455 A1* | 6/2008 | Hall et al. .................. 506/8 |
| 2009/0042203 A1 | 2/2009 | Koster |
| 2009/0047665 A1* | 2/2009 | Hall et al. .................. 435/5 |
| 2009/0092977 A1 | 4/2009 | Koster |

FOREIGN PATENT DOCUMENTS

| | | | |
|---|---|---|---|
| DE | 19852167 A1 | 5/2000 | |
| EP | 620862 B1 | 4/1998 | |
| EP | 1138782 A2 | 10/2001 | |
| EP | 1234888 A2 | 8/2002 | |
| EP | 1333101 A1 | 8/2003 | |
| EP | 1234888 A3 | 1/2004 | |
| GB | 2325002 A | 11/1998 | |
| GB | 2339905 A | 2/2000 | |
| WO | WO9015157 A1 | 12/1990 | |
| WO | WO9208117 A1 | 5/1992 | |
| WO | WO9209703 A1 | 6/1992 | |
| WO | WO9303186 A1 | 2/1993 | |
| WO | WO9305182 A1 | 3/1993 | |
| WO | WO9308297 A1 | 4/1993 | |
| WO | WO9416101 A2 | 7/1994 | |
| WO | WO9421822 A1 | 9/1994 | |
| WO | WO9504161 A1 | 2/1995 | |
| WO | WO9513396 A2 | 5/1995 | |
| WO | WO9629431 A2 | 9/1996 | |
| WO | WO9632504 A2 | 10/1996 | |
| WO | WO9635450 A1 | 11/1996 | |
| WO | WO9637630 A1 | 11/1996 | |
| WO | WO9733000 A1 | 9/1997 | |
| WO | WO9737041 A2 | 10/1997 | |
| WO | WO9803684 A1 | 1/1998 | |
| WO | WO9812355 A1 | 3/1998 | |
| WO | WO9814616 A1 | 4/1998 | |
| WO | WO9815652 A1 | 4/1998 | |
| WO | WO9820020 A2 | 5/1998 | |
| WO | WO9820157 A2 | 5/1998 | |
| WO | WO9820166 A2 | 5/1998 | |
| WO | WO9826095 A1 | 6/1998 | |
| WO | WO9831830 A1 | 7/1998 | |
| WO | WO9840520 A1 | 9/1998 | |
| WO | WO9854751 A1 | 12/1998 | |
| WO | WO9905319 A2 | 2/1999 | |
| WO | WO9912040 A2 | 3/1999 | |
| WO | WO9929898 A2 | 6/1999 | |
| WO | WO9957318 A2 | 11/1999 | |
| WO | WO0107648 A1 | 2/2001 | |
| WO | WO0123604 A2 | 4/2001 | |
| WO | WO0132930 A1 | 5/2001 | |
| WO | WO0151661 A2 | 7/2001 | |
| WO | WO0157263 A1 | 8/2001 | |
| WO | WO0157518 A2 | 8/2001 | |
| WO | WO0173199 A1 | 10/2001 | |
| WO | WO0210186 A1 | 2/2002 | |
| WO | WO0210444 A1 | 2/2002 | |
| WO | WO0218641 A2 | 3/2002 | |
| WO | WO0221108 A2 | 3/2002 | |
| WO | WO0222873 A1 | 3/2002 | |
| WO | WO0250307 A1 | 6/2002 | |
| WO | WO02057491 A2 | 7/2002 | |
| WO | WO02070664 A2 | 9/2002 | |
| WO | WO02077278 A1 | 10/2002 | |
| WO | WO02099034 A2 | 12/2002 | |
| WO | WO03002750 A2 | 1/2003 | |
| WO | WO03008636 A2 | 1/2003 | |
| WO | WO03016546 A1 | 2/2003 | |
| WO | WO03060163 A2 | 7/2003 | |
| WO | WO03088979 A2 | 10/2003 | |
| WO | WO03093506 A2 | 11/2003 | |
| WO | WO03097869 A2 | 11/2003 | |
| WO | WO03102191 A1 | 12/2003 | |
| WO | WO2004013357 A2 | 2/2004 | |
| WO | 2004060278 A2 | 7/2004 | |
| WO | 2007086935 A2 | 8/2007 | |
| WO | WO2007086904 A2 | 8/2007 | |
| WO | WO 2007086935 A2 * | 8/2007 | |
| WO | 2009017023 A1 | 2/2009 | |
| WO | 2009155103 A2 | 12/2009 | |
| WO | WO 2009155103 A2 * | 12/2009 | |

OTHER PUBLICATIONS

Metzker (Sequencing technologies—the next generation, Nature Rev. Genetics, vol. 11, Jan. 2010).*
Mardis (Next-Generation DNA Sequencing Methods, Annu. Rev. Genomics Hum. Genet., 9:387-402, Jun. 24, 2008).*
McGinnis et al. (BLAST: at the core of a powerful and diverse set of sequence analysis tools, Nucleic Acids Research, 2004, vol. 32).*
Li et al. (A survey of sequence alignment algorithms for next-generation sequencing, Briefings in Bioinformatics, vol. 11, No. 5, 473-483, May 11, 2010).*

(56) References Cited

OTHER PUBLICATIONS

Voelkerding et al. (Next-Generation Sequencing: From Basic Research to Diagnostics, Clinical Chemistry 55:4, 641-658, Feb. 26, 2009).*
Gupta (Single-molecule DNA sequencing technologies for future genomics research, Trends in Biotechnology vol. 26 No. 11, Aug. 21, 2008).*
Merriam-Webster, definition of "in silico," attached, accessed Oct. 13, 2014.*
Merriam-Webster, definition of "classify," attached, accessed Oct. 13, 2014.*
Extented European Search Report for Application No. EP10807255, mailed on Apr. 19, 2013, 8 pages.
Voelkerding K.V., et al., "Next-Generation Sequencing: from Basic Research to Diagnostics," Clinical Chemistry, 2009, vol. 55 (4), pp. 641-658.
Aaserud D.J., et al., "Accurate Base Composition of Double-Strand DNA by Mass Spectrometry," American Society for Mass Spectrometry, 1996, vol. 7 (12), pp. 1266-1269.
Alves-Silva J., et al., "The Ancestry of Brazilian mtDNA Linages," The American Journal of Human Genetics, 2000, vol. 67 (2), pp. 444-461.
Anderson S., et al., "Sequence and Organization of the Human Mitochondrial Genome," Nature, 1981, vol. 290 (5806), pp. 457-465.
Andreasson H., et al., "Mitochondrial Sequence Analysis for Forensic Identification Using Pyrosequencing Technology," BioTechniques, 2002, vol. 32 (1), pp. 124-133.
Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.
Baker G.C., et al., "Review and Re-Analysis of Domain-Specific 16S Primers," Journal of Microbiological Methods, 2003, vol. 55 (3), pp. 541-555.
Barbour A.G., et al., "Identification of an Uncultivatable *Borrelia* Species in the Hard Tick *Amblyomma americanum*: Possible Agent of a Lyme Disease-Like Illness," The Journal of Infectious Diseases, 1996, vol. 173 (2), pp. 403-409.
Barns S.M., et al., "Detection of Diverse New Francisella-like Bacteria in Environmental Samples," Applied and Environmental Microbiology, 2005, vol. 71 (9), pp. 5494-5500.
Barr I.G., et al., "An Influenza A(H3) Reassortant was Epidemic in Australia and New Zealand in 2003," Journal of Medical Virology, 2005, vol. 76 (3), pp. 391-397.
Batey R.T., et al., "Preparation of Isotopically Labeled Ribonucleotides for Multidimensional NMR Spectroscopy of RNA," Nucleic Acids Research, 1992, vol. 20 (17), pp. 4515-4523.
Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.
Benson L.M., et al, "Advantages of *Thermococcus kodakaraenis* (KOD) DNA Polymerase for PCR-Mass Spectrometry Based Analyses," American Society for Mass Spectrometry, 2003, vol. 14 (6), pp. 601-604.
Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.
Boivin-Jahns V., et al., "Bacterial Diversity in a Deep-Subsurface Clay Environment," Applied and Environmental Microbiology, 1996, vol. 62 (9), pp. 3405-3412.
Borrow R., et al., "SiaD PCR Elisa for Confirmation and Identification of Serogroup Y and W135 Meningococcal Infections," FEMS Microbiology Letters, 1998, vol. 159 (2), pp. 209-214.
Buck G.A., et al., "Design Strategies and Performance of Custom DNA Sequencing Primers," BioTechniques, 1999, vol. 27 (3), pp. 528-536.

Carracedo A., et al., "DNA Commission of the International Society for Forensic Genetics: Guidelines Formitochondrial DNA Typing," Forensic Science International, 2000, vol. 110 (2), pp. 79-85.
Case J.T., et al., "Maternal Inheritance of Mitochondrial DNA Polymorphisms in Cultured Human Fibroblasts," Somatic Cell Genetics, 1981, vol. 7 (1), pp. 103-108.
Chang P.K., et al., "aflT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chen C.H., et al., Laser Desorption Mass Spectrometry for FastDNA Sequencing [online], Nov. 1994, Retrieved from the Internet< URL:http://www.ornl.gove/sci/techresources/Human_Genome/publicat/94SANTA/sequencing/seqtoc.shtml>.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to 1.1 X 108 Daltons) by Electrospray Ionization FTICR MS," 42nd ASMS Conference on Mass Spectrometry, 1994.
Co-pending U.S. Appl. No. 90/010,209, filed Jun. 27, 2008.
Co-pending U.S. Appl. No. 90/010,210, filed Jun. 27, 2008.
Crespillo M., et al., "Mitochondrial DNA Sequences for 118 Individuals from Northeastern Spain," International Journal of Legal Medicine, 2000, vol. 114 (1-2), pp. 130-132.
De La Puente-Redondo V.A., et al., "Comparison of Different PCR Approaches for Typing of *Francisella tularensis* Strains," Journal of Clinical Microbiology, 2000, vol. 38 (3), pp. 1016-1022.
Del Blanco Garcia N., et al., "Genotyping of *Francisella tularensis* Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
DNA Database of Japan "Proliferative Kidney Organism 52134 18S Small Subunit Ribosomal RNA Gene." Accession No. U70623, Retrieved on Nov. 1, 2010.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Ecker Supporting Information [online], May 23, 2005 [retrieved on Jul. 31, 2011]. Retrieved from the Internet< URL: http://www.pnas.org/content/102/22/8012/suppl/DC1>.
Elnifro E.M., et al., "PCR and Restriction Endonuclease Analysis for Rapid Identification of Adenovirus Subgenera," Journal of Clinical Microbiology, 2000, vol. 38 (6), pp. 2055-2061.
EMBL "Human, muscle, Mitochondrial Mutant, 22 nt, segment 2 of 2," Accession No. S90302, Sep. 1, 2004.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Farlow J., et al., "*Francisella tularensis* Strain Typing Using Multiple-Locus, Variable-Number Tandem Repeat Analysis," Journal of Critical Microbiology, 2001, vol. 39 (9), pp. 3186-3192.
Final Office Action mailed Oct. 14, 2009 for U.S. Appl. No. 10/943,344, filed Sep. 17, 2004.

(56) References Cited

OTHER PUBLICATIONS

Fraser C.M., et al., "The Mimimal Gene Complement of *Mycoplasma genitalium*," Science, 1995, vol. 270 (5235), pp. 397-403.

Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.

Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.

Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.

Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.

GenBank, "*Clostridium tetani* E88, Complete Genome," Accession No. AE015927.1, Feb. 4, 2003.

GenBank, "*Enterococcus malodoratus* Strain ATCC43197 Elongation Factor Tu (tufA) Gene, Partial Cds," Accession No. AF274728, Dec. 11, 2000.

GenBank "*Staphylococcus aureus* Strain MSSA476, Complete Genome," Accession No. BX571857.1, Jun. 24, 2004.

GenBank, "*Staphylococcus epidermidis* ATCC 12228, Complete Genome," Accession No. AE015929.1, Jan. 2, 2003.

GenBank "*Streptococcus agalactiae* 2603V/R, Complete Genome," Accession No. AE009948.1, Aug. 28, 2002.

GenBank, "*Streptococcus anginosus* Elongation Factor Tu (tuf) Gene, Partial cds," Accession No. AF276257.1, Jul. 1, 2001.

GenBank, "*Streptococcus pyogenes* Strain MGAS8232, Complete Genome," Accession No. AE009949.1, Apr. 3, 2002.

Gendel S.M., "Computational Analysis of the Specificity of 16S rRNA-Derived Signature Sequencesfor Identifying Food-Related Microbes," Food Microbiology, 1996, vol. 13, pp. 1-15.

Giles R.E., et al., "Maternal Inheritance of Human Mitochondrial DNA," Proceedings of the National Academy of Sciences, 1980, vol. 77 (11), pp. 6715-6719.

Ginther C., et al., "Identifying Individuals by Sequencing Mitochondrial DNA from Teeth," Nature Genetics, 1992, vol. 2 (2), pp. 135-138.

Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.

Greenberg B.D., et al., "Intraspecific Nucleotide Sequence Variability Surrounding the Origin of Replicationin Human Mitochondrial DNA," Gene, 1983, vol. 21, pp. 33-49.

Griffin T.J., et al., "Single-Nucleotide Polymorphism Analysis by Maldi-TOF Mass Spectrometry," Trends in Biotechnology, 2000, vol. 18 (2), pp. 77-84.

Grzybowski T., et al., "Extremely High Levels of Human Mitochondrial DNA Heteroplasmy in Single Hair Roots," Electrophoresis, 2000, vol. 21 (3), pp. 548-553.

Gupta P.K., "Single-Molecule DNA Sequencing Technologies for Future Genomics Research," Trends in Biotechnology, 2008, vol. 26 (11), pp. 602-611.

Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.

Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.

Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.

Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.

Haugland R.A., et al., "Identification of Putative Sequence Specific PCR Primers for Detection of the Toxygenic Fungal Species *Stachybotrys chartarum*," Molecular and Cellular Probes, 1998, vol. 12 (6), pp. 387-396.

Hofstadler S.A., et al., "TIGER: The Universal Biosensor," International Journal of Mass Spectrometry, 2005, vol. 242, pp. 23-41.

Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.

Holm L., et al., "Removing Near-Neighbour Redundancy from Large Protein Sequence Collections," Bioinformatics, 1998, vol. 14 (5), pp. 423-429.

Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.

Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.

Hurst G.B., et al., "MALDI-TOF Analysis of Polymerase Chain Reaction Products from Methanotrophic Bacteria," Analytical Chemistry, 1998, vol. 70 (13), pp. 2693-2698.

Hutchison C.A., et al., "Maternal Inheritance of Mammalian Mitochondrial DNA," Nature, 1974, vol. 251 (5475), pp. 536-538.

Ingman M., et al., "Mitochondrial Genome Variation and the Origin of Modern Humans," Nature, 2000, vol. 408 (6813), pp. 708-713.

International Preliminary Report on Patentability for Application No. PCT/US2010/044774, mailed on Feb. 7, 2012, 1 page.

International Search Report and Written Opinion for Application No. PCT/US2010/044774, mailed on Jun. 17, 2011, 12 pages.

International Search Report for Application No. PCT/US2009/045635, mailed on Oct. 7, 2009, 9 pages.

Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.

Jackson P.E., et al., "Mass Spectrometry for Genotyping: an Emerging Tool for Molecular Medicine," Molecular Medicine Today, 2000, vol. 6 (7), pp. 271-276.

James A.M., et al., "*Borelia lonestari* Infection after a Bite by an *Amblyomma americanum* Tick," The Journal of Infectious Diseases, 2001, vol. 183 (12), pp. 1810-1814.

Jankowski K., et al., "Mass Spectrometry of DNA. Part 2 Quantitative Estimation of Base Composition," European Journal of Mass Spectrometry, 1980, vol. 1 (1), pp. 45-52.

Jansen R.C., et al., "Genotype-by-environment Interaction in Genetic Mapping of Multiple Quantitative Trait Loci," Theoretical and Applied Genetics, 1995, vol. 91, pp. 33-37.

Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.

Jiang C., et al., "Multiple Trait Analysis of Genetic Mapping for Quantitative Trait Loci Genetics," Genetics, 1995, vol. 140 (3), pp. 1111-1127.

(56) References Cited

OTHER PUBLICATIONS

Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.

Johansson A., et al., "Evaluation of PCR-based Methods for Discrimination of *Francisella* species and Subspecies and Development of a Specific PCR that Distinguishes the Two Major Subspecies of *Francisella tularensis*," Journal of Clinical Microbiology, 2000, vol. 38 (11), pp. 4180-4185.

Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.

Johnson Y.A., et al., "Precise Molecular Weight Determination of PCR Products of the rRNA Intergenic Spacer Region Using Electrospray Quadrupole Mass Spectrometry for Differentiation of *B. subtilis* and *B. atrophaeus*, Closely Related Species of Bacilli," Journal of Microbiological Methods, 2000, vol. 40 (3), pp. 241-254.

Ju J., et al., "Four-Color DNA Sequencing by Synthesis using Cleavable Fluorescent Nucleotide Reversible Terminators," Proceedings of the National Academy of Sciences, 2006, vol. 103 (52), pp. 19635-19640.

Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.

Jurinke C., et al., "Detection of Hepatitis B: Virus DNA in Serum Samples Via Nested PCR and MALDI-TOF Mass Spectrometry," Genetic Analysis: Biomolecular Engineering, 1996, vol. 13 (3), pp. 67-71.

Jurinke C., et al., "MALDI-TOF Mass Spectrometry. A Versatile Tool for High-Performance DNA Analysis," Molecular Biotechnology, 2004, vol. 26 (2), pp. 147-163.

Ke D., et al., "Development of a PCR Assay for Rapid Detection of *Enterococci*," Journal of Clinical Microbiology, 1999, vol. 37 (11), pp. 3497-3503.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Kilpatrick D.R., et al., "Group-Specific Identification of Polioviruses by PCR Using Primer Containing Mixed- Base or Deoxyinosine Residues at Positions of Codon Degeneracy," Journal of Clinical Microbiology, 1996, vol. 34 (12), pp. 2990-2996.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.

Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.

Li J., et al., "Single Nucleotide Polymorphism Determination Using Primer Extension and Time-of-Flight Mass Spectrometry," Electrophoresis, 1999, vol. 20 (6), pp. 1258-1265.

Limbach P.A., et al., "Enzymatic Sequencing of Oligonucleotides with Electrospray Mass Spectrometry," 42nd ASMS Conference on Mass Spectrometry, 1994.

Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.

Liu C., et al., "Improving the Microdialysis Procedure for Electrospray Ionization Mass Spectrometry of Biological Samples," Journal of Mass Spectrometry, 1997, vol. 32 (4), pp. 425-431.

Lubman D.M., Application for Continuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Matray T.J., et al., "Synthesis and Properties of RNA Analogs—Oligoribonucleotide N3->p5 Phosphoramidates," Nucleic Acids Research, 1999, vol. 27 (20), pp. 3976-3985.

McLafferty F.W., et al., "Comparison of Algorithms and Databases for Matching Unknown Mass Spectra," Journal of the American Society for Mass Spectrometry, 1998, vol. 9 (1), pp. 92-95.

McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.

Miller K.W., et al., "A Compendium of Human Mitochondria! DNA Control Region: Development of an International Standard Forensic Database," Croatian Medical Journal, 2001, vol. 42 (3), pp. 315-327.

Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.

Muddiman D.C., et al., "Characterization of PCR Products from Bacilli Using Electrospray Ionization FTICR Mass Spectrometry," Analytical Chemistry, 1996, vol. 68 (21), pp. 3705-3712.

Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.

Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.

Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.

Nakao H., et al., "Development of a Direct PCR Assay for Detection of the Diphtheria Toxin Gene," Journal of Clinical Microbiology, 1997, vol. 35 (7), pp. 1651-1655.

Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.

Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.

Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.

(56) References Cited

OTHER PUBLICATIONS

Nilsson M., et al., "Evaluation of Mitochondrial DNA Coding Region Assays for Increased Discrimination in Forensic Analysis," Forensic Science International: Genetics, 2008, vol. 2 (1), pp. 1-8.

Nishikawa T., et al., "Reconstitution of Active Recombinant Ship Toxin (Stc)1 from Recombinant Stxl-A and Sbtl-B Subunits Independently Produced by *E. coli* Clones," FEMS Microbiol Letters, 1999, vol. 178 (1), pp. 13-18.

Norder H., et al., "Typing of Hepatitis B Virus Genomes by a Simplified Polymerase Chain Reaction," Journal of Medical Virology, 1990, vol. 31 (3), pp. 215-221.

Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.

Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.

Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.

Null A.P., et al., "Evaluation of Sample Preparation Techniques for Mass Measurements of PCR Products Using ESIFT-ICR Mass Spectrometry," The American Society for Mass Spectrometry, 2002, vol. 13 (4), pp. 338-344.

Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.

Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.

Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.

Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.

Office Action mailed May 4, 2010 for U.S. Appl. No. 90/010,447 filed Apr. 9, 2009.
Office Action mailed May 4, 2010 for U.S. Appl. No. 90/010,448 filed Apr. 9, 2009.
Office Action mailed Dec. 9, 2009 for U.S. Appl. No. 90/010,210 filed Jun. 27, 2008.
Office Action mailed Dec. 9, 2009 for U.S. Appl. No. 90/010,447 filed Apr. 9, 2009.
Office Action mailed Dec. 9, 2009 for U.S. Appl. No. 90/010,448 filed Apr. 9, 2009.
Office Action mailed Jun. 10, 2009 for U.S. Appl. No. 90/010,210 filed Jun. 27, 2008.
Office Action mailed Jun. 10, 2010 for U.S. Appl. No. 90/010,447 filed Apr. 9, 2009.
Office Action mailed Jun. 10, 2010 for U.S. Appl. No. 90/010,448 filed Apr. 9, 2009.
Office Action mailed Aug. 11, 2010 for U.S. Appl. No. 90/010,447 filed Apr. 9, 2009.
Office Action mailed Aug. 11, 2010 for U.S. Appl. No. 90/010,448 filed Apr. 9, 2009.
Office Action mailed Jun. 11, 2010 for U.S. Appl. No. 90/010,210 filed Jun. 27, 2008.
Office Action mailed Apr. 16, 2009 for U.S. Appl. No. 90/010,210 filed Jun. 27, 2008.
Office Action mailed Sep. 20, 2010 for U.S. Appl. No. 90/010,447 filed Apr. 9, 2009.
Office Action mailed Sep. 20, 2010 for U.S. Appl. No. 90/010,448 filed Apr. 9, 2009.
Office Action mailed Apr. 21, 2009 for U.S. Appl. No. 90/010,209 filed Jun. 27, 2008.
Office Action mailed Jul. 22, 2008 for U.S. Appl. No. 90/010,209 filed Jun. 27, 2008.
Office Action mailed Jul. 22, 2008 for U.S. Appl. No. 90/010,210 filed Jun. 27, 2008.
Office Action mailed Apr. 23, 2010 for U.S. Appl. No. 90/010,210 filed Jun. 27, 2008.
Office Action mailed Apr. 24, 2009 for U.S. Appl. No. 90/010,447 filed Apr. 9, 2009.
Office Action mailed Apr. 24, 2009 for U.S. Appl. No. 90/010,448 filed Apr. 9, 2009.
Office Action mailed Aug. 24, 2010 for U.S. Appl. No. 90/010,210 filed Jun. 27, 2008.
Office Action mailed Nov. 24, 2009 for U.S. Appl. No. 90/010,210 filed Jun. 27, 2008.
Office Action mailed Sep. 24, 2009 for U.S. Appl. No. 90/010,210 filed Jun. 27, 2008.
Office Action mailed Jun. 25, 2009 for U.S. Appl. No. 90/010,210 filed Jun. 27, 2008.
Office Action mailed Jul. 28, 2010 for U.S. Appl. No. 90/010,210 filed Jun. 27, 2008.
Office Action mailed Oct. 29, 2009 for U.S. Appl. No. 90/010,447 filed Apr. 9, 2009.
Office Action mailed Oct. 29, 2009 for U.S. Appl. No. 90/010,448 filed Apr. 9, 2009.
Office Action mailed Jun. 30, 2010 for U.S. Appl. No. 90/010,210 filed Jun. 27, 2008.
Office Action mailed Jun. 30, 2010 for U.S. Appl. No. 90/010,447 filed Apr. 9, 2009.
Office Action mailed Jun. 30, 2010 for U.S. Appl. No. 90/010,448 filed Apr. 9, 2009.

Olsen B., et al., "Transhemispheric Exchange of Lyme Disease Spyrochetes by Seabirds," Journal of Clinical Microbiology, 1995, vol. 33 (12), pp. 3270-3274.

Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.

Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.

Pieles U., et al., "Matrix-Assisted Laser Desorption Ionization Time-of-Flight Spectrometry: A Powerful Tool for the Mass and Sequence Analysis of Natural and Modified Oligonucleotides," Nucleic Acids Research, 1993, vol. 21 (14), pp. 3191-3196.

Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.

Sampath R., et al., "Global Surveillance of Emerging Influenza Virus Genotypes by Mass Spectrometry," Plos ONE, 2007, vol. 2 (5), pp. e489.

Sampath R., et al., "Rapid Identification of Emerging Infectious Agents using PCR and Electrospray Ionization Mass Spectrometry," Annals of the New York Academy of Science, 2007, vol. 1102, pp. 109-120.

Sampath R., et al., "Rapid Identification of Emerging Pathogens: Coronavirus," Emerging Infectious Diseases, 2005, vol. 11 (3), pp. 373-379.

Sauer S., et al., "A Novel Procedure for Efficient Genotyping of Single Nucleotide Polymorphisms," Nucleic Acids Research, 2000, vol. 28 (5), pp. E13.1-E13.8.

Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.

(56) References Cited

OTHER PUBLICATIONS

Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Schena M., et al., "Genome Analysis with Gene Expression Microarrays," Bioessays, 1996, vol. 18 (5), pp. 427-431.
Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.
Sciacchitano C.J., "Analysis of Polymerase Chain Reaction-Amplified DNA Fragments of *Clostridium botulinum* Type E Neurotoxin Gene by High Performance Capillary Electrophoresis," Journal of Liquid Chromatography & Related Technologies, 1996, vol. 19 (13), pp. 2165-2178.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.
Supplementary European Search Report for Application No. EP05753037, mailed on Aug. 21, 2009, 2 pages.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assisted Laser Desorption/Ionization, 42nd ASMS Conference on Mass Spectrometry, 1994.
Tang K., et al., "Matrix-Assisted Laser Desorption/Ionization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Torroni A., et al., "Classification of European mtDNAs from an Analysis of Three European Populations," Genetics, 1996, vol. 144 (4), pp. 1835-1850.
Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.
Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.
Udo E.E., et al., "Genetic Analysis of Methicillin-Resistant *Staphylococcus aureus* Expressing High- and Low-Level Mupirocin Resistance," Journal of Medical Microbiology, 2001, vol. 50 (10), pp. 909-915.
Udo E.E., et al., "Rapid Detection of Methicillin Resistance in Staphylococci Using a Slide Latex Agglutination Kit," International Journal of Antimicrobial Agents, 2000, vol. 15 (1), pp. 19-24.
Unal S., et al., "Detection of Methicillin-Resistant Staphylococci by Using the Polymerase Chain Reaction," Journal of Clinical Microbiology, 1992, vol. 30 (7), pp. 1685-1691.
Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.
Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.
Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.
Van Ert M.N., et al., "Mass Spectrometry Provides Accurate Characterization of Two Genetic Marker Types in *Bacillus anthracis*," Bio Techniques, 2004, vol. 37 (4), pp. 642-651.
Vanderhallen H., et al., "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.
Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.
Widjojoatmodjo M.N., et al., "The Magnetic Immuno Polymerase Chain Reaction Assay for Direct Detection of *Salmonellae* in Fecal Samples," Journal of Clinical Microbiology, 1992, vol. 30 (12), pp. 3195-3199.
Xu L., et al., "Electrophore Mass Tag Dideoxy DNA Sequencing," Analytical Chemistry, 1997, vol. 69 (17), pp. 3595-3602.
Yao Z.P., et al., "Mass Spectrometry Based Proteolytic Mapping for Rapid Virus Identification," Analytical Chemistry, 2002, vol. 74 (11), pp. 2529-2534.
Zeng Z.B., "Precision Mapping of Quantitative Trait Loci," Genetics, 1994, vol. 136 (4), pp. 1457-1468.
Office Action mailed Jan. 15, 2014 for European Application No. EP10807255.4 filed Aug. 6, 2010.

* cited by examiner

FIGURE 2

Exemplary Amplicon Analysis

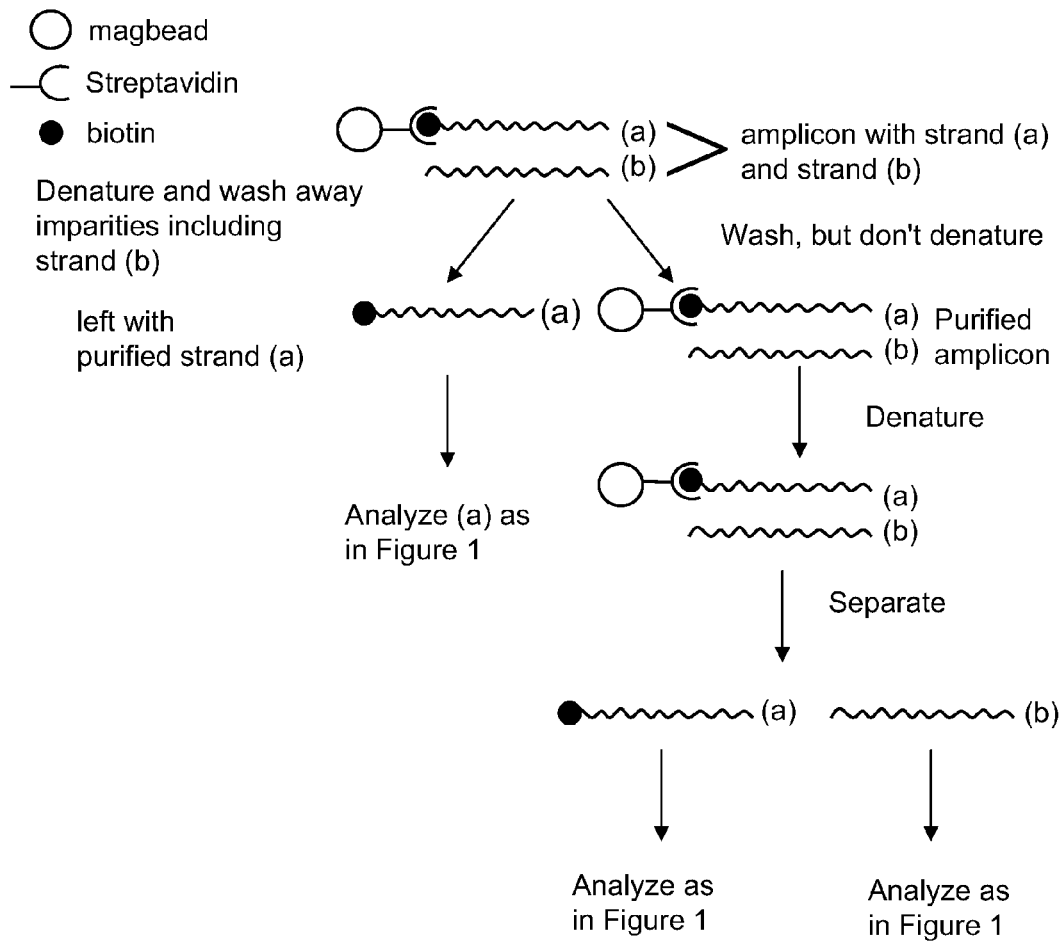

Note: When both amplicon strands are analyzed and only partial base counts determined, in certain cases complete base counts can be derived. For example, if one counts the number of As and Gs in both strands, then the number of Ts and Cs in the corresponding opposite strands are also known without the T or C nucleotides having been labeled or detected.

US 9,080,209 B2

NON-MASS DETERMINED BASE COMPOSITIONS FOR NUCLEIC ACID DETECTION

CROSS-REFERENCE TO RELATED APPLICATION

The present application is a national phase application under 35 U.S.C. §371 of PCT International Application No. PCT/US2010/044774, filed on 6 Aug. 2010, which claims priority to U.S. Provisional Patent Application Ser. No. 61/231,907 filed 6 Aug. 2009 each of which are herein incorporated by reference in their entirety.

FIELD OF THE INVENTION

The present invention relates to systems, methods, and compositions for nucleic acid detection based on non-mass determined base compositions. For example, in certain embodiments, base count data for a template nucleic acid is generated using an approach that does not measure molecular mass of the template nucleic acid (e.g., by sequencing the template nucleic acid) and a database comprising base count entries is queried to identify the target nucleic acid. In particular embodiments, sequencing is employed which is conducted in substantially real-time.

BACKGROUND OF THE INVENTION

In the United States, hospitals report well over 5 million cases of recognized infectious disease-related illnesses annually. Significantly greater numbers remain undetected, both in the inpatient and community setting, resulting in substantial morbidity and mortality. Critical intervention for infectious disease relies on rapid, sensitive and specific detection of the offending pathogen, and is central to the mission of microbiology laboratories at medical centers. Unfortunately, despite the recognition that outcomes from infectious illnesses are directly associated with time to pathogen recognition, as well as accurate identification of the class and species of microbe, and ability to identify the presence of drug resistance isolates, conventional hospital laboratories often remain encumbered by traditional slow multi-step culture based assays. Other limitations of the conventional laboratory which have become increasingly apparent include: extremely prolonged wait-times for pathogens with long generation time (up to several weeks); requirements for additional testing and wait times for speciation and identification of antimicrobial resistance; diminished test sensitivity for patients who have received antibiotics; and absolute inability to culture certain pathogens in disease states associated with microbial infection.

For more than a decade, molecular testing has been heralded as the diagnostic tool for the new millennium, whose ultimate potential could include forced obsolescence of traditional hospital laboratories. However, despite the fact that significant advances in clinical application of nucleic acid amplification techniques have occurred, the practicing physician still relies principally on standard techniques, such as culturing. As such, what is needed are rapid sensitive diagnostics systems and methods.

SUMMARY OF THE INVENTION

The present invention provides systems, methods, and compositions for nucleic acid detection based on non-mass determined base compositions. For example, in certain embodiments, base count data for a template nucleic acid is generated using an approach that does not measure molecular mass of the template nucleic acid (e.g., by sequencing the template nucleic acid) and a database comprising base count entries is queried to identify the target nucleic acid. Essentially any sequencing approach is optionally utilized in the present invention, including, for example, pyrosequencing, zero-mode waveguide type sequencing, nanopore sequencing, and the like. In particular embodiments, sequencing is employed which is conducted in substantially real-time.

In some embodiments, the present invention provides methods of identifying a template nucleic acid comprising: (a) determining at least a partial base count (e.g., a partial base count or a full base count) of at least a subsequence (e.g., a sub-sequence or a full sequence) of at least one template nucleic acid and/or a complement thereof, using an approach that does not measure molecular mass (e.g., without using mass spectrometry type methods) of the template nucleic acid, to produce base count data; and (b) querying a database comprising at least one base count entry (e.g., comprising 1 ... 5 ... 10 ... 100 ... 1000 ... 10,000 ... 50,000 ... or more base count entries) corresponding to an identified nucleic acid to produce a match of the base count data with the base count entry, thereby identifying the template nucleic acid.

In certain embodiments, the base count or partial base count is determined by sequencing. In other embodiments, the base count or partial base count is determined by liquid chromatography, such as High Performance Liquid Chromatography (HPLC). In further embodiments, the base count or partial base count is determined by paper chromatography (e.g., 2-D paper chromatography).

In particular embodiments, at least a partial base count only includes the number of A's present in a template nucleic acid (e.g., $A_{14}$). In particular embodiments, at least a partial base count only includes the number of C's present in a template nucleic acid (e.g., $C_{17}$). In particular embodiments, at least a partial base count only includes the number of G's present in a template nucleic acid (e.g., $G_{10}$). In particular embodiments, at least a partial base count only includes the number of T's present in a template nucleic acid (e.g., $T_{19}$). In other embodiments, at least a partial base count only includes two of the canonical bases (e.g., $A_{14}$, $C_{17}$). In further embodiments, at least a partial base count only includes three of the canonical bases (e.g., $A_{14}$, $C_{17}$, $G_{10}$). In additional exemplary embodiments, at least a partial base count includes all four canonical bases (e.g., $A_{14}$, $C_{17}$, $G_{10}$, $T_{19}$).

In certain embodiments, the template nucleic acid comprises DNA or RNA. In other embodiments, the determining is performed in real-time or substantially real-time (e.g., using a device comprising a zero-mode waveguide). In particular embodiments, the template nucleic acid comprises a mammalian nucleic acid, a bacterial nucleic acid, a viral nucleic acid, a fungal nucleic acid, or a protozoal nucleic acid. In further embodiments, the template nucleic acid is attached to a solid support. In additional embodiments, the methods further comprise amplifying the template nucleic acid prior to or during (a). In certain embodiments, the method further comprise obtaining the template nucleic acid from one or more sample sources selected from the group consisting of an environmental sample and a sample derived from a subject.

In particular embodiments, step (a) comprises contacting the template nucleic acid with at least one nucleotide incorporating biocatalyst, labeled nucleotides, and at least one primer nucleic acid that is at least partially complementary to at least a subsequence of the template nucleic acid, under conditions whereby the nucleotide incorporating biocatalyst extends the primer nucleic acid to produce an extended primer nucleic acid by incorporating the labeled nucleotides at a terminal end of the extended primer nucleic acid, wherein nucleotides that comprise different nucleobases comprise different labels, wherein the different labels produce detectable signals as or after the labeled nucleotides are incorporated at the terminal end of the extended primer nucleic acid, which detectable signals identify the labeled nucleotides incorporated at the terminal end of the extended primer nucleic acid and/or complementary nucleotides in the template nucleic acid, and wherein the detectable signals are detected as or after the labeled nucleotides are incorporated at the terminal end of the extended primer nucleic acid to thereby determine the base count of the subsequence of the template nucleic acid and/or the complement thereof. In other embodiments, the labels comprise different fluorescent labels and wherein the detectable signals are detected using a fluorescence microscope. In some embodiments, the at least one primer nucleic acid is a primer pair, wherein the primer pair is configured to hybridize with conserved regions of the two or more different bioagents and flank variable regions of the two or more different bioagents.

In particular embodiments, the terminal end of the extended primer nucleic acid is the 3' terminal end. In further embodiments, the nucleotide incorporating biocatalyst comprises an enzyme selected from the group consisting of: a polymerase, a terminal transferase, a reverse transcriptase, a polynucleotide phosphorylase, and a telomerase. In additional embodiments, the nucleotide incorporating biocatalyst comprises one or more modifications. In some embodiments, the nucleotide incorporating biocatalyst is an enzyme derived from an organism that is selected from the group consisting of: *Thermus antranikianii, Thermus aquaticus, Thermus caldophilus, Thermus chliarophilus, Thermus filiformis, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Anaerocellum thermophilum, Bacillus caldotenax,* and *Bacillus stearothermophilus.*

In certain embodiments, the nucleotide incorporating biocatalyst comprises a Φ29 DNA polymerase. In other embodiments, a label is attached to one of a heterocyclic base of a labeled nucleotide, a sugar moiety of a labeled nucleotide, and a phosphate group of a labeled nucleotide. In further embodiments, a linker attaches a label to a labeled nucleotide. In particular embodiments, the extended primer nucleic acid is complementary to a subsequence of the template nucleic acid. In further embodiments, the extended primer nucleic acid is complementary to a full-length sequence of the template nucleic acid. In certain embodiments, the primer nucleic acid comprises an intelligent primer. In other embodiments, the label comprises a fluorescent dye, a non-fluorescent label, a colorimetric label, a chemiluminescent label, a bioluminescent label, a radioisotope, an antibody, an antigen, biotin, a hapten, or an enzyme. In other embodiments, the label is a fluorescent dye selected from the group consisting of: a rhodamine dye, a fluorescein dye, a halofluorescein dye, a dichlororhodamine dye, an energy transfer dye, a Lucifer dye, Oregon Green, and a cyanine dye. In some embodiments, the label is a fluorescent dye selected from the group consisting of: JOE, VIC, TET, HEX, PAM, R6G, R110, TAMRA, and ROX. In particular embodiments, the label is a radioisotope selected from the group consisting of: $^3H$, $^{14}C$, $^{22}Na$, $^{32}P$, $^{33}P$, $^{35}S$, $^{42}K$, $^{45}Ca$, $^{59}Fe$, $^{125}I$, and $^{203}Hg$.

In certain embodiments, the methods comprise determining at least partial base counts of subsequences of two or more template nucleic acids and/or complements thereof, using an approach that does not measure molecular mass of the template nucleic acids to produce the base count data. In other embodiments, the methods comprise querying the database to produce two or more matches of the base count data with two or more base count entries to thereby identify the template nucleic acid. In other embodiments, identifying the template nucleic acid comprises identifying an organismal source of the template nucleic acid and/or one or more properties of the template nucleic acid. In some embodiments, the properties of the template nucleic acid comprise a genotype, a virulence property, a pathogenic property, and/or a drug resistance property. In particular embodiments, the determining is performed in substantially real-time.

In other embodiments, the organismal source comprises a mammal, a bacterium, a virus, a fungus, or a protozoan. In further embodiments, the organismal source is identified at one or more taxonomic rank levels selected from the group consisting of: a Domain, a Superphylum, a Superdivision, a Superclass, a Superorder, a Superfamily, a Superspecies, a Kingdom, a Phylum, a Division, a Class, a Legion, an Order, a Family, a Tribe, a Genus, a Species, a Subkingdom, a Subphylum, a Subclass, a Cohort, a Suborder, a Subfamily, a Subtribe, a Subgenus, a Subspecies, an Infrakingdom, a Branch, an Infraphylum, an Infraclass, an Infraorder, an Alliance, an Infraspecies, a Microphylum, a Parvclass, and a Parvorder.

In some embodiments, the present invention provides systems comprising: at least one sequencing device; at least one primer pair configured to hybridize with conserved regions of two or more different bioagents and flank variable regions of the two or more different bioagents; and a computer readable medium having one or more logic instructions for directing a system to: (a) determine at least a partial base count of at least a subsequence of at least one template nucleic acid and/or a complement thereof, using an approach that does not measure molecular mass of the template nucleic acid, to produce base count data; and (b) query a database comprising at least one base count entry corresponding to an identified nucleic acid to produce a match of the base count data with the base count entry to thereby identifying the template nucleic acid.

In certain embodiments, the system comprise instructions for determining at least a partial base count of at least a subsequence of at least one template nucleic acid and/or a complement thereof, in substantially real-time without measuring the molecular mass of the template nucleic acid to produce base count data using the zero-mode waveguide and the primer nucleic acid and for identifying the template nucleic acid using the base count data. In certain embodiments, the sequencing device comprises a zero-mode waveguide. In other embodiments, the systems comprise at least one nucleotide incorporating biocatalyst and/or labeled nucleotides. In further embodiments, the systems further comprise one or more containers for packaging the zero-mode waveguide, or the primer pair.

In certain embodiments, the present invention provides a computer program product, comprising a computer readable medium having one or more logic instructions for directing a system to: (a) determine at least a partial base count of at least a subsequence of at least one template nucleic acid and/or a complement thereof (e.g., in substantially real-time), using an approach that does not measure molecular mass of the template nucleic acid, to produce base count data; and (b) query a database comprising at least one base count entry corresponding to an identified nucleic acid to produce a match of the base count data with the base count entry to thereby identifying the template nucleic acid.

In some embodiments, the present invention provides system comprising: a reaction vessel or substrate; a detector configured to detect detectable signals produced in or on the reaction vessel or substrate, which detectable signals correspond to at least some nucleobases incorporated into a nucleic acid to generate nucleobase incorporation data; a database of base count entries indexed to identified nucleic acids; and a controller configured to correlate the nucleobase incorporation data with detected base counts and to query the database for a match between the detected base counts and the base count entries to thereby identify or detect the nucleic acids.

In particular embodiments, the reaction vessel or substrate comprises at least one zero-mode waveguide. In further embodiments, the detector comprises a fluorescence microscope. In other embodiments, the systems comprise at least one material transfer component that transfers material to and/or from the reaction vessel or substrate. In other embodiments, the systems comprise at least one thermal modulator configured to modulate temperature in the reaction vessel or substrate. In other embodiments, the reaction vessel or substrate comprises at least one primer nucleic acid is selected from the primer nucleic acids disclosed in one or more of the published documents incorporated by reference herein. In other embodiments, the systems comprise at least one nucleic acid sample preparation component and/or at least one nucleic acid amplification component.

In further embodiments, the present invention provides methods of identifying a target nucleic acid in a sample comprising: (a) at least partially sequencing the target nucleic acid, or amplified sequences thereof, to generate sequence data; (b) determining at least a partial base count from the sequence data to generate base count data; and (c) querying a database comprising at least one base count entry corresponding to the target nucleic acid to produce a match of the base count data with the base count entry, thereby identifying the target nucleic acid.

In some embodiments, the present invention provides methods of identifying a target nucleic acid in a sample comprising: (a) amplifying one or more segments of the nucleic acid in the sample using at least one purified oligonucleotide primer pair to generate amplified sequences, wherein the primer pair is configured to hybridize with conserved regions of two or more different bioagents and flank variable regions of the two or more different bioagents; (b) at least partially sequencing the amplified sequences to generate sequence data; (c) determining at least a partial base count from the sequence data to generate base count data; and (d) querying a database comprising at least one base count entry corresponding to the target nucleic acid to produce a match of the base count data with the base count entry, thereby identifying the target nucleic acid.

In certain embodiments, the molecular mass of the target sequence or the amplified sequences is not determined in the identifying the target nucleic acid. In further embodiments, the sequencing is performed in real-time or substantially real-time. In other embodiments, the identifying the target nucleic acid is performed in substantially real-time. In further embodiments, the at least partially sequencing the target nucleic acid is performed with a device comprising at least one zero-mode waveguide. In some embodiments, the primer pair comprises forward and reverse primers that are about 20 to 35 nucleobases in length.

In other embodiments, the present invention provides systems comprising: (a) a sequencing device configured to generate nucleic acid sequence data corresponding to the nucleic acid sequence of one or more amplicons produced using at least one purified oligonucleotide primer pair that comprises forward and reverse primers, wherein the primer pair comprises nucleic acid sequences that are substantially complementary to nucleic acid sequences of two or more different bioagents; and (b) a controller operably connected to the sequencing device, the controller configured to: i) determine at least a partial base count from the nucleic acid sequence data to generate base count data, and ii) query a database with the base count data, wherein the database comprises at least one base count entry corresponding to a target nucleic acid.

In certain embodiments, the database comprises base composition information (entries) for at least three different bioagents. In other embodiments, the database comprises base composition information for at least 2 . . . 10 . . . 50 . . . 100 . . . 1000 . . . 10,000, or 100,000 different bioagents. In some embodiments, the base composition data comprises at least 10 . . . 50 . . . 100 . . . 500 . . . 1000 . . . 1000 . . . 10,000 . . . or 100,000 unique base compositions. In further embodiments, the database is stored on a local computer. In particular embodiments, the database is accessed from a remote computer over a network. In further embodiments, the base composition information in the database is associated with bioagent identity. In certain embodiments, the base composition data in the database is associated with bioagent geographic origin.

In some embodiments, the present invention provides methods of identifying a target nucleic acid in a sample comprising: (a) amplifying one or more segments of the target nucleic acid in the sample using at least one purified oligonucleotide primer pair to generate a sample comprising amplified sequences, wherein said primer pair comprises a forward primer and a reverse primer and is configured to hybridize with conserved regions of two or more different bioagents and flank variable regions of the two or more different bioagents; (b) treating the sample with reagents such that the amplified sequences in the sample are digested into monodeoxynucleosides; (c) quantitating the monodeoxynucleosides using HPLC, paper chromatography, or similar non-mass spectrometry based technique such that base count data is generated; and (f) querying a database comprising at least one base count entry corresponding to the target nucleic acid to produce a match of the base count data with said base count entry, thereby identifying the target nucleic acid. In certain embodiments, the methods further comprise a step after step (a) but before step (b) of treating the sample comprising amplified sequences such that either the sense strands corresponding to the forward primer or said anti-sense strands corresponding to the reverse primer of the amplified sequences are removed from the sample in order to generate a purified sample. In certain embodiments, step (c) employs a phosphodiesterase (e.g., such as snake venom phosphodiesterase I).

BRIEF DESCRIPTION OF THE DRAWINGS

The foregoing summary and detailed description is better understood when read in conjunction with the accompanying drawings which are included by way of example and not by way of limitation.

FIG. 2 shows one embodiment of a bioagent identification process of the present invention.

DETAILED DESCRIPTION OF EMBODIMENTS

The present invention provides systems, methods, and compositions for nucleic acid detection based on non-mass determined base compositions. For example, in certain embodiments, base count data for a template nucleic acid is generated without measuring the molecular mass of the template nucleic acid (e.g., by sequencing the template nucleic acid) and a database comprising base count entries is queried to identify the target nucleic acid. In particular embodiments, sequencing is employed which is conducted in substantially real-time.

The present invention provides methods that are useful in detecting and characterizing nucleic acids. The methods typically involve determining at least partial base counts (i.e., partial or complete base counts) and/or the sequence of template or target nucleic acids in real-time without measuring the molecular mass of the template nucleic acid. Exemplary applications of the method include diagnosing infectious or genetic diseases, forensics, genotyping, and companion diagnostics, among many other applications. In addition, the invention also provides related zero-mode waveguide (e.g., arrays of zero-mode waveguides), kits, computer program products and systems.

The term "partial base composition" or "partial base count" refers to the number of each residue of at least one nucleobase type (e.g., a given purine nucleobase type, a given pyrimidine nucleobase type, a given nucleobase analog type, and/or the like), but not each residue comprised in an amplicon or other nucleic acid (e.g., for single or multiple strands of those nucleic acids), without consideration for the linear arrangement of these residues in the strand(s) of the amplicon. For example, if a given amplicon or other nucleic acid includes four nucleobase types (e.g., adenosine (A), guanosine (G), cytidine, (C), and (deoxy)thymidine (T)), a partial base count for that amplicon or other nucleic acid would include the number of any one of those four nucleobase types (e.g., $[A_w]$, $[G_x]$, $[C_y]$, or $[T_z]$), any two of those four nucleobase types (e.g., $[A_wG_x]$, $[A_wC_y]$, $[A_wT_z]$, $[G_xC_y]$, $[G_xT_z]$, or $[C_yT_z]$), or at most any three of those four nucleobase types (e.g., $[A_wG_xC_y]$, $[A_wC_yT_z]$, $[A_wG_xT_z]$, or $[G_xC_yT_z]$), in which w, x, y and z are each independently a whole number representing the number of said nucleoside residues in that amplicon or other nucleic acid. To further illustrate, if a nucleic acid has the following composition: ATTGCCTAAGGTTAACG, then partial base counts for that nucleic acid include $[A_5]$, $[G_4]$, $[C_3]$, $[T_5]$, $[A_5G_4]$, $[A_5C_3]$, $[A_5T_5]$, $[G_4C_3]$, $[G_4T_5]$, $[C_3T_5]$, $[A_5G_4C_3]$, $[A_5C_3T_5]$, $[A_5G_4T_5]$, or $[G_4C_3T_5]$.

Figure 1:
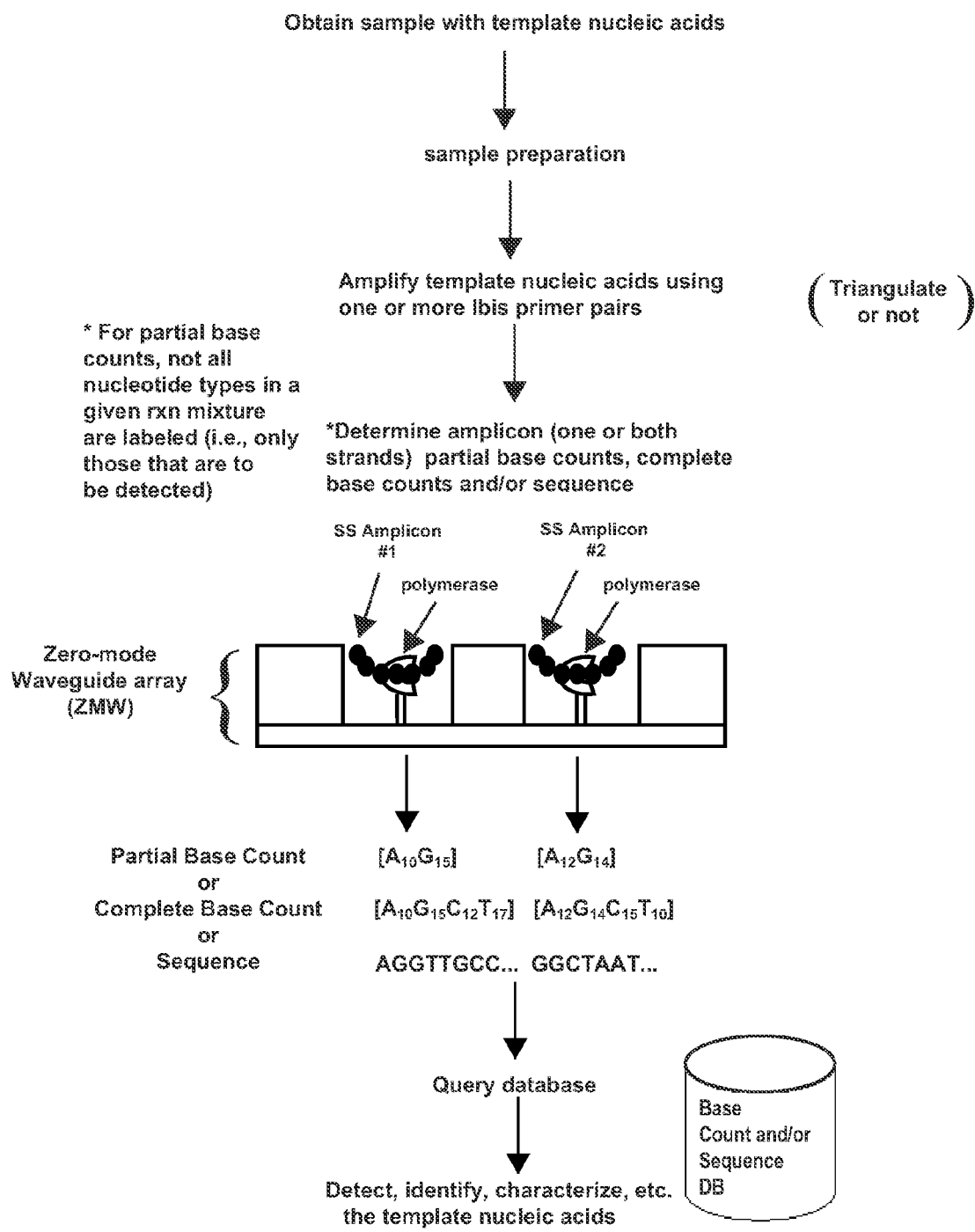
FIG. 1 shows one embodiment of a bioagent identification process of the present invention.

FIG. 1 schematically illustrates an exemplary process according to one embodiment of the invention. As shown, the process includes obtaining a sample with template nucleic acids. The sample is prepared, for example, by purifying or at partially isolating the template nucleic acids. As shown, the template nucleic acids are amplified, for example, in polymerase chain reactions or other amplification approaches to produce amplicons. In some embodiments, template nucleic acids are analyzed directly, for example, without being amplified. Amplicon base counts and/or sequences are determined, for example, using an array of zero-mode waveguides and a fluorescent microscope (and, e.g., primer nucleic acids (e.g., intelligent primers), polymerases (e.g., Φ29 DNA polymerases, etc.), phospholinked nucleotides, etc, as also described in, for example, Korlach et al. (2008) "Selective aluminum passivation for targeted immobilization of single DNA polymerase molecules in zero-mode waveguide nanostructures" Proc. Nat'l. Acad. Sci. U.S.A. 105(4):1176-1181, herein incorporated by reference. The determined amplicon base counts and/or amplicon sequence information is used to query a base counts and/or sequence database to detect, identify, characterize, etc. the template nucleic acids. See also, FIG. 2 for additional exemplary variations.

Sequencing Technologies

As described above, embodiments of the present invention involve determining the base composition, or partial base composition, or a target sequence without determining the mass of the target sequence (e.g., without using mass spectrometry related methods). In certain embodiments, such methods of determining base compositions employ sequencing methods. The present invention is not limited by the type of sequencing method employed. Exemplary sequencing methods are described below.

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A set of methods referred to as "next-generation sequencing" techniques have emerged as alternatives to Sanger and dye-terminator sequencing methods (Voelkerding et al., *Clinical Chem.*, 55: 641-658, 2009; MacLean et al., *Nature Rev. Microbiol.*, 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1 \times 10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color and thus identity of each probe corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally reconstructed, and template bases are interrogated twice, resulting in increased accuracy. Sequence read length averages 35 nucleotides, and overall output exceeds 4 billion bases per sequencing run.

In certain embodiments, nanopore sequencing in employed (see, e.g., Astier et al., J Am Chem Soc. 2006 Feb. 8; 128(5):1705-10, herein incorporated by reference). The theory behind nanopore sequencing has to do with what occurs when the nanopore is immersed in a conducting fluid and a potential (voltage) is applied across it: under these conditions a slight electric current due to conduction of ions through the nanopore can be observed, and the amount of current is exceedingly sensitive to the size of the nanopore. If DNA molecules pass (or part of the DNA molecule passes) through the nanopore, this can create a change in the magnitude of the current through the nanopore, thereby allowing the sequences of the DNA molecule to be determined.

HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety) is the first commercialized single-molecule sequencing platform. This method does not require clonal amplification. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

Another exemplary nucleic acid sequencing approach developed by Stratos Genomics, Inc. that is also optionally adapted for use with the present invention involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Patent Publication No. 20090035777, entitled "HIGH THROUGHPUT NUCLEIC ACID SEQUENCING BY EXPANSION," that was filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-658, 2009; U.S. Pat. No. 7,329,492; U.S. patent application. Ser. No. 11/671,956; U.S. patent application Ser. No. 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., *Clinical Chem.*, 55: 641-658, 2009; MacLean et al., *Nature Rev. Microbiol.*, 7: 287-296; U.S. Pat. No. 7,170,050; U.S. Pat. No. 7,302,146; U.S. Pat. No. 7,313,308; U.S. Pat. No. 7,476,503; all of which are herein incorporated by reference) utilizes reaction wells 50-100 nm in diameter and encompassing a reaction volume of approximately 20 zeptoliters ($10 \times 10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters (10-21 liters). At this volume, the activity of a single molecule can be detected amongst a background of thousands of labeled nucleotides.

The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

As the DNA polymerase incorporates complementary nucleotides, each base is held within the detection volume for tens of milliseconds, which is orders of magnitude longer than the amount of time it takes a nucleotide to diffuse in and out of the detection volume. During this time, the engaged fluorophore emits fluorescent light whose color corresponds to the base identity. Then, as part of the natural incorporation cycle, the polymerase cleaves the bond holding the fluorophore in place and the dye diffuses out of the detection volume. Following incorporation, the signal immediately returns to baseline and the process repeats.

Unhampered and uninterrupted, the DNA polymerase continues incorporating bases at a speed of tens per second. In this way, a completely natural long chain of DNA is produced in minutes. Simultaneous and continuous detection occurs across all of the thousands of ZMWs on the SMRT chip in real time. This approach has the capability to produce reads thousands of nucleotides in length.

Some aspects the invention are generally directed to optical detection or monitoring systems (e.g., ZMVs discussed above), methods enabled by such systems, and components of such systems for monitoring, in real-time, optical signals that emanate from multiple discrete sources of those optical signals. In particular, the optical detection and monitoring systems are generally capable of monitoring discrete signals from potentially very large numbers of different signal sources, optionally separating and/or deconvolving such signals into constituent signal events, and doing so in real-time, despite that such signals may be changing rapidly, over time.

The systems typically include all or a portion of a collection of different functional elements. These elements include the multiple discrete sources that include the capability of generating optical signals. In some aspects, such sources include chemical, biochemical and/or biological reactants, or mimics of such reactants that are capable of generating optical signals that are indicative of their presence, reaction or conversion. While the sources may be capable of generating optical signals on their own, in certain cases, a source of excitation radiation is also provided to excite optical signals, e.g., fluorescence, within the sources.

The systems also typically include optical elements that direct, separate, and/or otherwise alter optical signals from these sources (as well as excitation radiation directed at such sources), in order to ultimately derive optimal amounts of information from such signals when they are ultimately detected. Consequently, the systems typically include an optical detection system for detecting the potentially large numbers of signals that were directed from the sources, and optionally separated and/or otherwise altered by the optical elements. Signals detected by the optical detection system are then recorded and processed by appropriate processing systems and data management processes to provide output of the system in user ready formats.

The systems are typically applied in the monitoring of arrays or collections of spatially discrete chemical, biochemical and/or biological reactions that generate optically detectable signals, such as chromogenic reactions, luminescent or luminogenic reactions, or fluorescent or fluorogenic reactions. A few examples of reactions include those that are regularly performed in the pharmaceutical, biotechnology and healthcare diagnostic fields, i.e., base count analyses, immunoassays, enzymatic assays, receptor assays, nucleic acid hybridization assays, nucleic acid synthesis reactions, cellular assays, and many others.

Typically, the progress of the reactions used in application of the systems described herein result in one or more of the consumption, production and/or conversion of a material that is capable of generating an optically detectable signal, either alone, or in response to an external stimulus, e.g., excitation radiation. By way of example, certain reactants may become fluorescent upon reaction with another reactant, or may have their fluorescence altered or reduced upon such reaction. As such, the fluorescence emitted from the reaction in response to an excitation radiation will change as the reaction progresses. The systems generally provide for the source of such signals, e.g., the area in which the reaction occurs, including optionally, the reactants and/or products, the optical elements for collecting, directing and optionally separating and/or altering such signals from such sources, and the ultimate detection of such signals, as well as the manipulation of the resulting data to yield optimal value and information for the user.

The systems typically include all or a subset of a substrate that includes all or a subset of the sources of optical signals, an optional excitation light source, an optical train that includes the various optical elements for collection, direction and/or manipulation of the optical signals and optional excitation light, optical detectors for receiving, detecting and recording (or putting into a form for recordation) the optical signals, as well as processors for processing data derived from the optical detectors.

Figure 3:
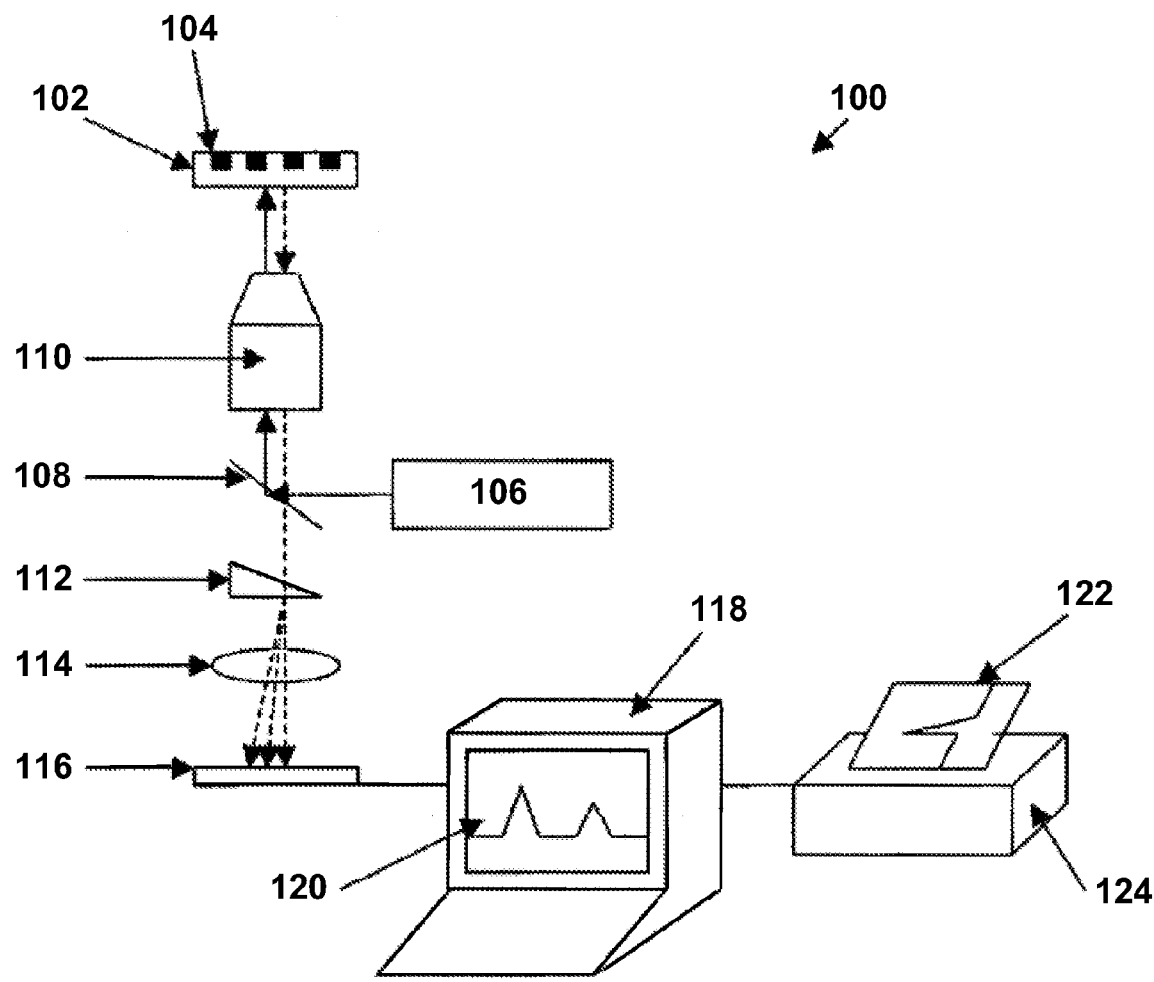
FIG. 3 shows one embodiment of a sequencing system composed of zero-move waveguides.

A general schematic representation of the system as set forth above, is illustrated in FIG. 3. As shown, the system 100 includes a substrate 102 that includes a plurality of discrete sources of optical signals, e.g., reaction wells or optical confinements 104. An excitation light source, e.g., laser 106, is optionally provided in the system and is positioned to direct excitation radiation at the various signal sources. This is typically done by directing excitation radiation at or through appropriate optical components, e.g., dichroic 108 and objective lens 110, that direct the excitation radiation at the substrate 102, and particularly the signal sources 104. Emitted signals from source 104 are then collected by the optical components, e.g., objective 110, and passed through additional optical elements, e.g., dichroic 108, prism 12 and lens 114, until they are directed to and impinge upon an optical detection system, e.g., detector array 116. The signals are then detected by detector array 116, and the data from that detection is transmitted to an appropriate data processing unit, e.g., computer 118, where the data is subjected to interpretation, analysis, and ultimately presented in a user ready format, e.g., on display 120, or printout 122, from printer 124.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al., U.S. Pat. No. 7,315,019, entitled "Arrays of optical confinements and uses thereof", issued Jan. 1, 2008 to Turner et al., U.S. Pat. No. 7,313,308, entitled "Optical analysis of molecules", issued Dec. 25, 2007 to Turner et al., U.S. Pat. No. 7,302,146, entitled "Apparatus and method for analysis of molecules", issued Nov. 27, 2007 to Turner et al., and U.S. Pat. No. 7,170,050, entitled "Apparatus and methods for optical analysis of molecules", issued Jan. 30, 2007 to Turner et al., U.S. Patent Publications Nos. 20080212960, entitled "Methods and systems for simultaneous real-time monitoring of optical signals from multiple sources", filed Oct. 26, 2007 by Lundquist et al., 20080206764, entitled "Flowcell system for single molecule detection", filed Oct. 26, 2007 by Williams et al., 20080199932, entitled "Active surface coupled polymerases", filed Oct. 26, 2007 by Hanzel et al., 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al., 20080176316, entitled "Mitigation of photodamage in analytical reactions", filed Oct. 31, 2007 by Eid et al., 20080176241, entitled "Mitigation of photodamage in analytical reactions", filed Oct. 31, 2007 by Eid et al., 20080165346, entitled "Methods and systems for simultaneous real-time monitoring of optical signals from multiple sources", filed Oct. 26, 2007 by Lundquist et al., 20080160531, entitled "Uniform surfaces for hybrid material substrates and methods for making and using same", filed Oct. 31, 2007 by Korlach, 20080157005, entitled "Methods and systems for simultaneous real-time monitoring of optical signals from multiple sources", filed Oct. 26, 2007 by Lundquist et al., 20080153100, entitled "Articles having localized molecules disposed thereon and methods of producing same", filed Oct. 31, 2007 by Rank et al., 20080153095, entitled "CHARGE SWITCH NUCLEOTIDES", filed Oct. 26, 2007 by Williams et al., 20080152281, entitled "Substrates, systems and methods for analyzing materials", filed Oct. 31, 2007 by Lundquist et al., 20080152280, entitled "Substrates, systems and methods for analyzing materials", filed Oct. 31, 2007 by Lundquist et al., 20080145278, entitled "Uniform surfaces for hybrid material substrates and methods for making and using same", filed Oct. 31, 2007 by Korlach, 20080128627, entitled "SUBSTRATES, SYSTEMS AND METHODS FOR ANALYZING MATERIALS", filed Aug. 31, 2007 by Lundquist et al., 20080108082, entitled "Polymerase enzymes and reagents for enhanced nucleic acid sequencing", filed Oct. 22, 2007 by Rank et al., 20080095488, entitled "SUBSTRATES FOR PERFORMING ANALYTICAL REACTIONS", filed Jun. 11, 2007 by Foquet et al., 20080080059, entitled "MODULAR OPTICAL COMPONENTS AND SYSTEMS INCORPORATING SAME", filed Sep. 27, 2007 by Dixon et al., 20080050747, entitled "Articles having localized molecules disposed thereon and methods of producing and using same", filed Aug. 14, 2007 by Korlach et al., 20080032301, entitled "Articles having localized molecules disposed thereon and methods of producing same", filed Mar. 29, 2007 by Rank et al., 20080030628, entitled "Methods and systems for simultaneous real-time monitoring of optical signals from multiple sources", filed Feb. 9, 2007 by Lundquist et al., 20080009007, entitled "CONTROLLED INITIATION OF PRIMER EXTENSION", filed Jun. 15, 2007 by Lyle et al., 20070238679, entitled "Articles having localized molecules disposed thereon and methods of producing same", filed Mar. 30, 2006 by Rank et al., 20070231804, entitled "Methods, systems and compositions for monitoring enzyme activity and applications thereof", filed Mar. 31, 2006 by Korlach et al., 20070206187, entitled "Methods and systems for simultaneous real-time monitoring of optical signals from multiple sources", filed Feb. 9, 2007 by Lundquist et al., 20070196846, entitled "Polymerases for nucleotide analogue incorporation", filed Dec. 21, 2006 by Hanzel et al., 20070188750, entitled "Methods and systems for simultaneous real-time monitoring of optical signals from multiple sources", filed Jul. 7, 2006 by Lundquist et al., 20070161017, entitled "MITIGATION OF PHOTODAMAGE IN ANALYTICAL REACTIONS", filed Dec. 1, 2006 by Eid et al., 20070141598, entitled "Nucleotide Compositions and Uses Thereof", filed Nov. 3, 2006 by Turner et al., 20070134128, entitled "Uniform surfaces for hybrid material substrate and methods for making and using same", filed Nov. 27, 2006 by Korlach, 20070128133, entitled "Mitigation of photodamage in analytical reactions", filed Dec. 2, 2005 by Eid et al., 20070077564, entitled "Reactive surfaces, substrates and methods of producing same", filed Sep. 30, 2005 by Roitman et al., 20070072196, entitled "Fluorescent nucleotide analogs and uses therefore", filed Sep. 29, 2005 by Xu et al., and 20070036511, entitled "Methods and systems for monitoring multiple optical signals from a single source", filed Aug. 11, 2005 by Lundquist et al., and Korlach et al. (2008) "Selective aluminum passivation for targeted immobilization of single DNA polymerase molecules in zero-mode waveguide nanostructures" Proc. Nat'l. Acad. Sci. U.S.A. 105(4): 11761181—all of which are herein incorporated by reference in their entireties.

DEFINITIONS AND FURTHER DESCRIPTION

It is to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

As used herein, the term "about" means encompassing plus or minus 10%. For example, about 200 nucleotides refers to a range encompassing between 180 and 220 nucleotides.

As used herein, the term "amplicon" or "bioagent identifying amplicon" refers to a nucleic acid generated using the primer pairs described herein. The amplicon is typically double stranded DNA; however, it may be RNA and/or DNA: RNA. In some embodiments, the amplicon comprises DNA complementary to HPV RNA, DNA, or cDNA. In some embodiments, the amplicon comprises sequences of conserved regions/primer pairs and intervening variable region. As discussed herein, primer pairs are configured to generate amplicons from bioagent nucleic acid. As such, the base composition of any given amplicon may include the primer pair, the complement of the primer pair, the conserved regions and the variable region from the bioagent that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used to generate the base composition data. Bioagent identifying amplicons generate base compositions that are preferably unique to the identity of a bioagent.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

The term "attached" refers to interactions including, but not limited to, covalent bonding, ionic bonding, chemisorption, physisorption, and combinations thereof.

As used herein, "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

As used herein, the term "base composition" or "base count" refers to the number of each residue comprised in an amplicon or other nucleic acid, without consideration for the linear arrangement of these residues in the strand(s) of the amplicon. The amplicon residues comprise, adenosine (A), guanosine (G), cytidine, (C), (deoxy)thymidine (T), uracil (U), inosine (I), nitroindoles such as 5-nitroindole or 3-nitropyrrole, dP or dK (Hill F et al. Polymerase recognition of synthetic oligodeoxyribonucleotides incorporating degenerate pyrimidine and purine bases. *Proc Natl Acad Sci USA*. 1998 Apr. 14; 95(8):4258-63), an acyclic nucleoside analog containing 5-nitroindazole (Van Aerschot et al., *Nucleosides and Nucleotides*, 1995, 14, 1053-1056), the purine analog 1-(2-deoxy-beta-D-ribofuranosyl)-imidazole-4-carboxamide, 2,6-diaminopurine, 5-propynyluracil, 5-propynylcytosine, phenoxazines, including G-clamp, 5-propynyl deoxycytidine, deoxy-thymidine nucleotides, 5-propynylcytidine, 5-propynyluridine and mass tag modified versions thereof, including 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$. In some, embodiments, the non-natural nucleosides used herein include 5-propynyluracil, 5-propynylcytosine and inosine. Herein the base composition for an unmodified DNA amplicon is notated as $A_wG_xC_yT_z$, wherein w, x, y and z are each independently a whole number representing the number of said nucleoside residues in an amplicon. Base compositions for amplicons comprising modified nucleosides are similarly notated to indicate the number of said natural and modified nucleosides in an amplicon.

As used herein, a "base composition probability cloud" is a representation of the diversity in base composition resulting from a variation in sequence that occurs among different isolates of a given species, family or genus. Base composition calculations for a plurality of amplicons are mapped on a pseudo four-dimensional plot. Related members in a family, genus or species typically cluster within this plot, forming a base composition probability cloud.

As used herein, the term "base composition signature" refers to the base composition generated by any one particular amplicon.

As used herein, a "bioagent" means any biological organism or component thereof or a sample containing a biological organism or component thereof, including microorganisms or infectious substances, or any naturally occurring, bioengineered or synthesized component of any such microorganism or infectious substance or any nucleic acid derived from any such microorganism or infectious substance. Those of ordinary skill in the art will understand fully what is meant by the term bioagent given the instant disclosure. Still, a non-exhaustive list of bioagents includes: cells, cell lines, human clinical samples, mammalian blood samples, cell cultures, bacterial cells, viruses, viroids, fungi, protists, parasites, rickettsiae, protozoa, animals, mammals or humans. Samples may be alive, non-replicating or dead or in a vegetative state (for example, vegetative bacteria or spores).

As used herein, a "bioagent division" is defined as group of bioagents above the species level and includes but is not limited to, orders, families, genus, classes, clades, genera or other such groupings of bioagents above the species level.

As used herein, "broad range survey primers" are primers designed to identify an unknown bioagent as a member of a particular biological division (e.g., an order, family, class, clade, or genus). However, in some cases the broad range survey primers are also able to identify unknown bioagents at the species or sub-species level. As used herein, "division-wide primers" are primers designed to identify a bioagent at the species level and "drill-down" primers are primers designed to identify a bioagent at the sub-species level. As used herein, the "sub-species" level of identification includes, but is not limited to, strains, subtypes, variants, and isolates. Drill-down primers are not always required for identification at the sub-species level because broad range survey intelligent primers may, in some cases provide sufficient identification resolution to accomplishing this identification objective. Broad range survey primers may be used in the non-mass determined base compositions methods and systems of the present invention.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "conserved region" in the context of nucleic acids refers to a nucleobase sequence (e.g., a subsequence of a nucleic acid, etc.) that is the same or similar in two or more different regions or segments of a given nucleic acid molecule (e.g., an intramolecular conserved region), or that is the same or similar in two or more different nucleic acid molecules (e.g., an intermolecular conserved region). To illustrate, a conserved region may be present in two or more different taxonomic ranks (e.g., two or more different genera, two or more different species, two or more different subspecies, and the like) or in two or more different nucleic acid molecules from the same organism. To further illustrate, in certain embodiments, nucleic acids comprising at least one conserved region typically have between about 70%-100%, between about 80-100%, between about 90-100%, between about 95-100%, or between about 99-100% sequence identity in that conserved region. A conserved region may also be selected or identified functionally as a region that permits generation of amplicons via primer extension through hybridization of a completely or partially complementary primer to the conserved region for each of the target sequences to which conserved region is conserved.

As used herein, in some embodiments the term "database" is used to refer to a collection of base composition and/or partial base composition data. The base composition data in the database is indexed to bioagents and to primer pairs. The base composition data reported in the database comprises the number of at least one type of nucleoside in an amplicon (e.g., $A_{17}$) that would be generated for each bioagent using each primer. The database can be populated by empirical data. In this aspect of populating the database, a bioagent is selected and a primer pair is used to generate an amplicon. Note that base composition entries in the database may be derived from sequencing data (i.e., known sequence information). An entry in the database is made to associate correlate the base composition with the bioagent and the primer pair used. The database may also be populated using other databases comprising bioagent information. For example, using the GenBank database it is possible to perform electronic PCR using an electronic representation of a primer pair. This in silico method may provide the base composition for any or all selected bioagent(s) stored in the GenBank database. The information may then be used to populate the base composition database as described above. A base composition database can be in silico, a written table, a reference book, a spreadsheet or any form generally amenable to databases. Preferably, it is in silico on computer readable media.

The term "detect", "detecting" or "detection" refers to an act of determining the existence or presence of one or more targets (e.g., bioagent nucleic acids, amplicons, etc.) in a sample.

As used herein, the term "etiology" refers to the causes or origins, of diseases or abnormal physiological conditions.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extended primer nucleic acid" refers to a primer nucleic acid to which one or more additional nucleotides have been added or otherwise incorporated (e.g., covalently bonded to).

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length sequence or fragment thereof are retained.

A "genotype" refers to all or part of the genetic constitution of a nucleic acid molecule, cell or subject, or group of nucleic acid molecules, cells or subjects. For example, a genotype includes the particular mutations and/or alleles (e.g., polymorphisms, such as single nucleotide polymorphisms (SNPs) or the like) present at a given locus or distributed in a genome.

A "heterocyclic ring" refers to a monocyclic or bicyclic ring that is either saturated, unsaturated, or aromatic, and which comprises one or more heteroatoms independently selected from nitrogen, oxygen and sulfur. A heterocyclic ring may be attached to the sugar moiety, or analog thereof, of a nucleotide of the invention via any heteroatom or carbon atom. Exemplary heterocyclic rings include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl, and the like.

A "homocyclic ring" refers to a saturated or unsaturated (but not aromatic) carbocyclic ring, such as cyclopropane, cyclobutane, cyclopentane, cyclohexane, cycloheptane, cyclohexene, and the like.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to nucleic acid sequences that are not found naturally associated with the gene sequences in the chromosome or are associated with portions of the chromosome not found in nature (e.g., genes expressed in loci where the gene is not normally expressed).

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. In context of the present invention, sequence identity is meant to be properly determined when the query sequence and the subject sequence are both described and aligned in the 5' to 3' direction. Sequence alignment algorithms such as BLAST, will return results in two different alignment orientations. In the Plus/Plus orientation, both the query sequence and the subject sequence are aligned in the 5' to 3' direction. On the other hand, in the Plus/Minus orientation, the query sequence is in the 5' to 3' direction while the subject sequence is in the 3' to 5' direction. It should be understood that with respect to the primers of the present invention, sequence identity is properly determined when the alignment is designated as Plus/Plus. Sequence identity may also encompass alternate or "modified" nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, "housekeeping gene" or "core viral gene" refers to a gene encoding a protein or RNA involved in basic functions required for survival and reproduction of a bioagent. Housekeeping genes include, but are not limited to, genes encoding RNA or proteins involved in translation, replication, recombination and repair, transcription, nucleotide metabolism, amino acid metabolism, lipid metabolism, energy generation, uptake, secretion and the like.

As used herein, the term "hybridization" or "hybridize" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, the melting temperature ($T_m$) of the formed hybrid, and the G:C ratio within the nucleic acids. A single molecule that contains pairing of complementary nucleic acids within its structure is said to be "self-hybridized." An extensive guide to nucleic hybridization may be found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993), which is incorporated by reference.

A "label" refers to a moiety attached (covalently or non-covalently), or capable of being attached, to a molecule, which moiety provides or is capable of providing information about the molecule (e.g., descriptive, identifying, etc. information about the molecule). Exemplary labels include fluorescent labels, non-fluorescent labels, colorimetric labels, chemiluminescent labels, bioluminescent labels, radioactive labels, mass-modifying groups, antibodies, antigens, biotin, haptens, and enzymes (including, e.g., peroxidase, phosphatase, etc.).

The term "kit" is used in reference to a combination of articles that facilitate a process, method, assay, analysis or manipulation of a sample. Kits can contain instructions describing how to use the kit (e.g., instructions describing the methods of the invention), zero-mode waveguides, primer nucleic acids, nucleotide incorporating biocatalysts, labeled nucleotides, chemical reagents, as well as any other components.

A "linker" or "spacer" refers to a chemical moiety that covalently or non-covalently (e.g., ionically, etc.) attaches a compound or substituent group to, e.g., a solid support, another compound or group, or the like. For example, a linker optionally attaches a label (e.g., a fluorescent dye, a radioisotope, etc.) to a nucleotide or the like. Linkers are typically bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support, another compound, etc. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Additional description of linker molecules is provided in, e.g., Lyttle et al. (1996) *Nucleic Acids Res.* 24(14):2793, Shchepino et al. (2001) *Nucleosides, Nucleotides, & Nucleic Acids* 20:369, Doronina et al. (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, Pljevaljcic et al. (2003) *J. Am. Chem. Soc.* 125(12):3486, Ward, et. al., U.S. Pat. No. 4,711,955, Stavrianopoulos, U.S. Pat. No. 4,707,352, and Stavrianopoulos, U.S. Pat. No. 4,707,440, which are each incorporated by reference.

A "mass modifying" group modifies the mass, typically measured in terms of molecular weight as daltons, of a molecule that comprises the group. For example, mass modifying groups that increase the discrimination between at least two nucleic acids with single base differences in size or sequence can be used to facilitate sequencing using, e.g., molecular weight determinations.

A "mixture" refers to a combination of two or more different components. A "reaction mixture" refers a mixture that comprises molecules that can participate in and/or facilitate a given reaction.

The term "molecular mass" refers to the mass of a compound (e.g., a nucleic acid, etc.) as determined, for example, using mass spectrometry.

A "modified" enzyme refers to an enzyme comprising a monomer sequence in which at least one monomer of the sequence differs from a monomer in a reference sequence, such as a native or wild-type form of the enzyme or another modified form of the enzyme, e.g., when the two sequences are aligned for maximum identity. Exemplary modifications include monomer insertions, deletions, and substitutions. The modified enzymes (i.e., protein- or nucleic acid-based catalysts) of the invention have been or are optionally created by various diversity generating methods. Although essentially any method can be used to produce a modified enzyme, certain exemplary techniques include recombining (e.g., via recursive recombination, synthetic recombination, or the like) two or more nucleic acids encoding one or more parental enzymes, or by mutating one or more nucleic acids that encode enzymes, e.g., using recursive ensemble mutagenesis, cassette mutagenesis, random mutagenesis, in vivo mutagenesis, site directed mutagenesis, or the like. A nucleic acid encoding a parental enzyme typically includes a gene that, through the mechanisms of transcription and translation, produces an amino acid sequence corresponding to a parental enzyme, e.g., a native form of the enzyme. Modified enzymes also include chimeric enzymes that have identifiable component sequences (e.g., structural and/or functional domains, etc.) derived from two or more parents. Also included within the definition of modified enzymes are those comprising chemical modifications (e.g., attached substituent groups, altered substituent groups, etc.) relative to a reference sequence.

A "moiety" or "group" refers to one of the portions into which something, such as a molecule, is divided (e.g., a functional group, substituent group, or the like). For example, a nucleotide typically comprises a basic group (e.g., adenine, thymine, cytosine, guanine, uracil, or an analog basic group), a sugar moiety (e.g., a moiety comprising a sugar ring or an analog thereof), and one or more phosphate groups.

As used herein, the term "primer" or "primer nucleic acid" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, "intelligent primers" or "primers" or "primer pairs," in some embodiments, are oligonucleotides that are designed to bind to conserved sequence regions of one or more bioagent nucleic acids to generate bioagent identifying amplicons. In some embodiments, the bound primers flank an intervening variable region between the conserved binding sequences. Upon amplification, the primer pairs yield amplicons e.g., amplification products that provide base composition variability between the two or more bioagents. The variability of the base compositions allows for the identification of one or more individual bioagents from, e.g., two or more bioagents based on the base composition distinctions. In some embodiments, the primer pairs are also configured to generate amplicons amenable to molecular mass analysis. Further, the sequences of the primer members of the primer pairs are not necessarily fully complementary to the conserved region of the reference bioagent. For example, in some embodiments, the sequences are designed to be "best fit" amongst a plurality of bioagents at these conserved binding sequences. Therefore, the primer members of the primer pairs have substantial complementarity with the conserved regions of the bioagents, including the reference bioagent.

In some embodiments of the invention, the oligonucleotide primer pairs described herein can be purified. As used herein, "purified oligonucleotide primer pair," "purified primer pair," or "purified" means an oligonucleotide primer pair that is chemically-synthesized to have a specific sequence and a specific number of linked nucleosides. This term is meant to explicitly exclude nucleotides that are generated at random to yield a mixture of several compounds of the same length each with randomly generated sequence. As used herein, the term "purified" or "to purify" refers to the removal of one or more components (e.g., contaminants) from a sample.

The term "nucleic acid" or "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-$N^6$-methyladenosine, aziridinylcytosine, pseudoisocytosine, 5-(carboxyhydroxyl-methyl)-uracil, 5-fluorouracil, 5-bromouracil, 5-carboxymethylaminomethyl-2-thiouracil, 5-carboxymethyl-aminomethyluracil, dihydrouracil, inosine, $N^6$-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, $N^6$-methyladenine, 7-methylguanine, 5-methylaminomethyluracil, 5-methoxy-amino-methyl-2-thiouracil, beta-D-mannosylqueosine, 5'-methoxycarbonyl-methyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP). As is used herein, a nucleobase includes natural and modified residues, as described herein.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.).

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid. Exemplary nucleotide incorporating enzymes include, e.g., DNA polymerases, RNA polymerases, terminal transferases, reverse transcriptases, telomerases, polynucleotide phosphorylases, and the like.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth Enzymol.* 68: 90-99; the phosphodiester method of Brown et al. (1979) *Meth Enzymol.* 68: 109-151; the diethylphosphoramidite method of Beaucage et al. (1981) *Tetrahedron Lett.* 22: 1859-1862; the triester method of Matteucci et al. (1981) *J Am Chem Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

As used herein, a "sample" refers to anything capable of being analyzed by the methods provided herein. In some embodiments, the sample comprises or is suspected to comprise one or more nucleic acids capable of analysis by the methods. Preferably, the samples comprise nucleic acids (e.g., DNA, RNA, cDNAs, etc.) from one or more bioagents. Samples can include, for example, blood, saliva, urine, feces, anorectal swabs, vaginal swabs, cervical swabs, and the like. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As is used herein, the term "single primer pair identification" means that one or more bioagents can be identified using a single primer pair. A base composition signature for an amplicon may singly identify one or more bioagents.

A "solid support" refers to a solid material which can be derivatized with, or otherwise attached to, a chemical moiety, such as a primer nucleic acid, a template nucleic acid, or the like. Exemplary solid supports include a zero-mode waveguide array, a plate, a bead, a microbead, a fiber, a whisker, a comb, a hybridization chip, a membrane, a single crystal, a ceramic layer, a self-assembling monolayer, and the like.

As used herein, a "sub-species characteristic" is a genetic characteristic that provides the means to distinguish two members of the same bioagent species. For example, one viral strain may be distinguished from another viral strain of the same species by possessing a genetic change (e.g., for example, a nucleotide deletion, addition or substitution) in one of the viral genes, such as the RNA-dependent RNA polymerase.

A "subsequence" or "fragment" refers to any portion of an entire nucleic acid sequence.

As used herein, in some embodiments the term "substantial complementarity" means that a primer member of a primer pair comprises between about 70%-100%, or between about 80-100%, or between about 90-100%, or between about 95-100%, or between about 99-100% complementarity with the conserved binding sequence of a nucleic acid from a given bioagent. These ranges of complementarity and identity are inclusive of all whole or partial numbers embraced within the recited range numbers. For example, and not limitation, 75.667%, 82%, 91.2435% and 97% complementarity or sequence identity are all numbers that fall within the above recited range of 70% to 100%, therefore forming a part of this description.

A "system" in the context of analytical instrumentation refers a group of objects and/or devices that form a network for performing a desired objective.

A "template nucleic acid" refers to a nucleic acid to which a primer nucleic acid can hybridize and be extended. Accordingly, template nucleic acids include subsequences that are at least partially complementary to the primer nucleic acids. Template nucleic acids can be derived from essentially any source. To illustrate, template nucleic acids are optionally derived or isolated from, e.g., cultured microorganisms, uncultured microorganisms, complex biological mixtures, tissues, sera, pooled sera or tissues, multispecies consortia, ancient, fossilized or other nonliving biological remains, environmental isolates, soils, groundwaters, waste facilities, deep-sea environments, or the like. Further, template nucleic acids optionally include or are derived from, e.g., individual cDNA molecules, cloned sets of cDNAs, cDNA libraries, extracted RNAs, natural RNAs, in vitro transcribed RNAs, characterized or uncharacterized genomic DNAs, cloned genomic DNAs, genomic DNA libraries, enzymatically fragmented DNAs or RNAs, chemically fragmented DNAs or RNAs, physically fragmented DNAs or RNAs, or the like. Template nucleic acids can also be chemically synthesized using techniques known in the art. In addition, template nucleic acids optionally correspond to at least a portion of a gene or are complementary thereto.

As used herein, "triangulation identification" means the use of more than one primer pair to generate a corresponding amplicon for identification of a bioagent. The more than one primer pair can be used in individual wells or vessels or in a multiplex PCR assay. Alternatively, PCR reactions may be carried out in single wells or vessels comprising a different primer pair in each well or vessel. Following amplification the amplicons are pooled into a single well or container which is then subjected to base composition analysis (e.g., which does not involve molecular mass analysis). The combination of pooled amplicons can be chosen such that the expected ranges of base compositions of individual amplicons are not overlapping and thus will not complicate identification of signals. Triangulation is a process of elimination, wherein a first primer pair identifies that an unknown bioagent may be one of a group of bioagents. Subsequent primer pairs are used in triangulation identification to further refine the identity of the bioagent amongst the subset of possibilities generated with the earlier primer pair. Triangulation identification is complete when the identity of the bioagent is determined. The triangulation identification process may also be used to reduce false negative and false positive signals, and enable reconstruction of the origin of hybrid or otherwise engineered bioagents. For example, identification of the three part toxin genes typical of *B. anthracis* (Bowen et al., *J Appl Microbiol.*, 1999, 87, 270-278) in the absence of the expected compositions from the *B. anthracis* genome would suggest a genetic engineering event.

As used herein, the term "unknown bioagent" can mean, for example: (i) a bioagent whose existence is not known (for example, the SARS coronavirus was unknown prior to April 2003) and/or (ii) a bioagent whose existence is known (such as the well known bacterial species *Staphylococcus aureus* for example) but which is not known to be in a sample to be analyzed. For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, the second meaning (ii) of "unknown" bioagent would apply because the SARS coronavirus became known to science subsequent to April 2003 because it was not known what bioagent was present in the sample.

As used herein, the term "variable region" is used to describe a region that falls between any one primer pair described herein. The region possesses distinct base compositions between at least two bioagents, such that at least one bioagent can be identified at, for example, the family, genus, species or sub-species level. The degree of variability between the at least two bioagents need only be sufficient to allow for identification using mass spectrometry analysis, as described herein.

As used herein, a "wobble base" is a variation in a codon found at the third nucleotide position of a DNA triplet. Variations in conserved regions of sequence are often found at the third nucleotide position due to redundancy in the amino acid code.

In certain embodiments, provided herein are methods, compositions, kits, and related systems for the detection and identification of bioagents (e.g., species of HPV) using bioagent identifying amplicons. In some embodiments, primers are selected to hybridize to conserved sequence regions of nucleic acids derived from a bioagent and which flank variable sequence regions to yield a bioagent identifying amplicon which can be amplified and which is amenable to base composition analysis. In some embodiments, the corresponding base composition of one or more different amplicons is queried against a database of base compositions indexed to bioagents and to the primer pair used to generate the amplicon. A match of the measured base composition to a database entry base composition associates the sample bioagent to an indexed bioagent in the database. Thus, the identity of the unknown bioagent is determined. No prior knowledge of the unknown bioagent is necessary to make an identification. In some instances, the measured base composition associates with more than one database entry base composition. Thus, a second/subsequent primer pair is generally used to generate an amplicon, and its measured base composition is similarly compared to the database to determine its identity in triangulation identification. Furthermore, the methods and other aspects of the invention can be applied to rapid parallel multiplex analyses, the results of which can be employed in a triangulation identification strategy. Thus, in some embodiments, the present invention provides rapid throughput and does not require nucleic acid sequencing or knowledge of the linear sequences of nucleobases of the amplified target sequence for bioagent detection and identification.

Methods of employing base compositions, databases containing base composition entries, and triangulation using primers, are described in the following patents, patent applications and scientific publications, all of which are herein incorporated by reference as if fully set forth herein: U.S. Pat. Nos. 7,108,974; 7,217,510; 7,226,739; 7,255,992; 7,312,036; 7,339,051; US patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/116263; WO2005/

117270; WO2006/019784; WO2006/034294; WO2006/071241; WO2006/094238; WO2006/116127; WO2006/135400; WO2007/014045; WO2007/047778; WO2007/086904; WO2007/100397; and WO2007/118222, all of which are herein incorporated by reference.

Exemplary base-count related methods and other aspects of use in the methods, systems, and other aspects of the invention are also described in, for example, Ecker et al., Ibis T5000: a universal biosensor approach for microbiology. Nat Rev Microbiol. 2008 Jun. 3; Ecker et al., The Microbial Rosetta Stone Database: A compilation of global and emerging infectious microorganisms and bioterrorist threat agents; Ecker et al., The Ibis T5000 Universal Biosensor: An Automated Platform for Pathogen Identification and Strain Typing; Ecker et al., The Microbial Rosetta Stone Database: A common structure for microbial biosecurity threat agents; Ecker et al., Identification of *Acinetobacter* species and genotyping of *Acinetobacter baumannii* by multilocus PCR and mass spectrometry. *J Clin Microbiol.* 2006 August; 44(8): 2921-32; Ecker et al., Rapid identification and strain-typing of respiratory pathogens for epidemic surveillance. *Proc Natl Acad Sci USA.* 2005 May 31; 102(22):8012-7. Epub 2005 May 23; Wortmann et al., Genotypic evolution of *Acinetobacter* baumannii Strains in an outbreak associated with war trauma, *Infect Control Hosp Epidemiol.* 2008 June; 29(6): 553-555; Hannis et al., High-resolution genotyping of *Campylobacter* species by use of PCR and high-throughput mass spectrometry. *J Clin Microbiol.* 2008 April; 46(4): 1220-5; Blyn et al., Rapid detection and molecular serotyping of adenovirus by use of PCR followed by electrospray ionization mass spectrometry. *J Clin Microbiol.* 2008 February; 46(2):644-51; Eshoo et al., Direct broad-range detection of alphaviruses in mosquito extracts, *Virology,* 2007 Nov. 25; 368(2):286-95; Sampath et al., Global surveillance of emerging Influenza virus genotypes by mass spectrometry. *PLoS ONE.* 2007 May 30; 2(5):e489; Sampath et al., Rapid identification of emerging infectious agents using PCR and electrospray ionization mass spectrometry. *Ann N Y Acad Sci.* 2007 April; 1102: 109-20; Hujer et al., Analysis of antibiotic resistance genes in multidrug-resistant *Acinetobacter* sp. isolates from military and civilian patients treated at the Walter Reed Army Medical Center. *Antimicrob Agents Chemother.* 2006 December; 50(12):4114-23; Hall et al., Base composition analysis of human mitochondrial DNA using electrospray ionization mass spectrometry: a novel tool for the identification and differentiation of humans. *Anal Biochem.* 2005 Sep. 1; 344(1):53-69; Sampath et al., Rapid identification of emerging pathogens: coronavirus. *Emerg Infect Dis.* 2005 March; 11(3):373-9; Jiang Y, Hofstadler S A. A highly efficient and automated method of purifying and desalting PCR products for analysis by electrospray ionization mass spectrometry; Jiang et al., Mitochondrial DNA mutation detection by electrospray mass spectrometry; Russell et al., Transmission dynamics and prospective environmental sampling of adenovirus in a military recruit setting; Hofstadler et al., Detection of microbial agents using broad-range PCR with detection by mass spectrometry: The TIGER concept. Chapter in; Hofstadler et al., Selective ion filtering by digital thresholding: A method to unwind complex ESI-mass spectra and eliminate signals from low molecular weight chemical noise; Hofstadler et al., TIGER: The Universal Biosensor; Van Ert et al., Mass spectrometry provides accurate characterization of two genetic marker types in *Bacillus anthracis*; Sampath et al., Forum on Microbial Threats: Learning from SARS: Preparing for the Next Disease Outbreak—Workshop Summary (ed. Knobler S E, Mahmoud A, Lemon S.) The National Academies Press, Washington, D.C. 2004.181-185.

In some embodiments, amplicons corresponding to bioagent identifying amplicons are obtained using the polymerase chain reaction (PCR). Other amplification methods may be used such as ligase chain reaction (LCR), low-stringency single primer PCR, and multiple strand displacement amplification (MDA). (Michael, S F., *Biotechniques* (1994), 16:411-412 and Dean et al., *Proc. Natl. Acad. Sci. U.S.A.* (2002), 99, 5261-5266).

Figure 4:
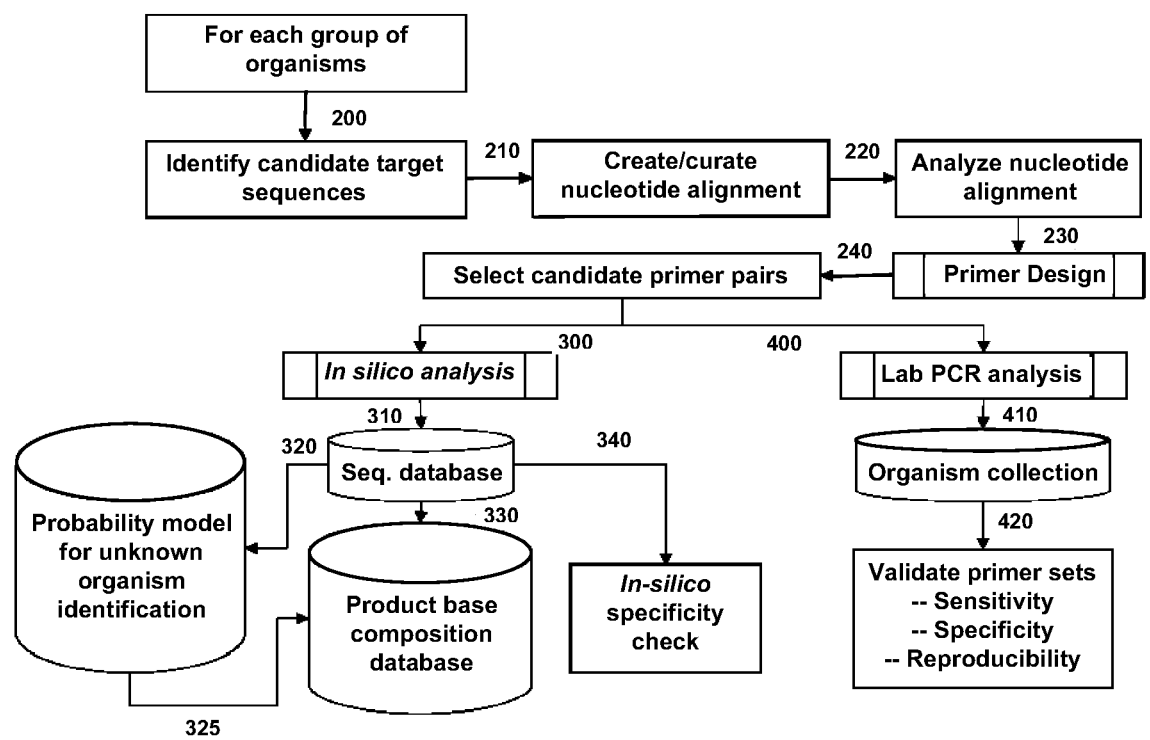
FIG. 4 shows a process diagram illustrating one embodiment of the primer pair selection process.
Figure 5:
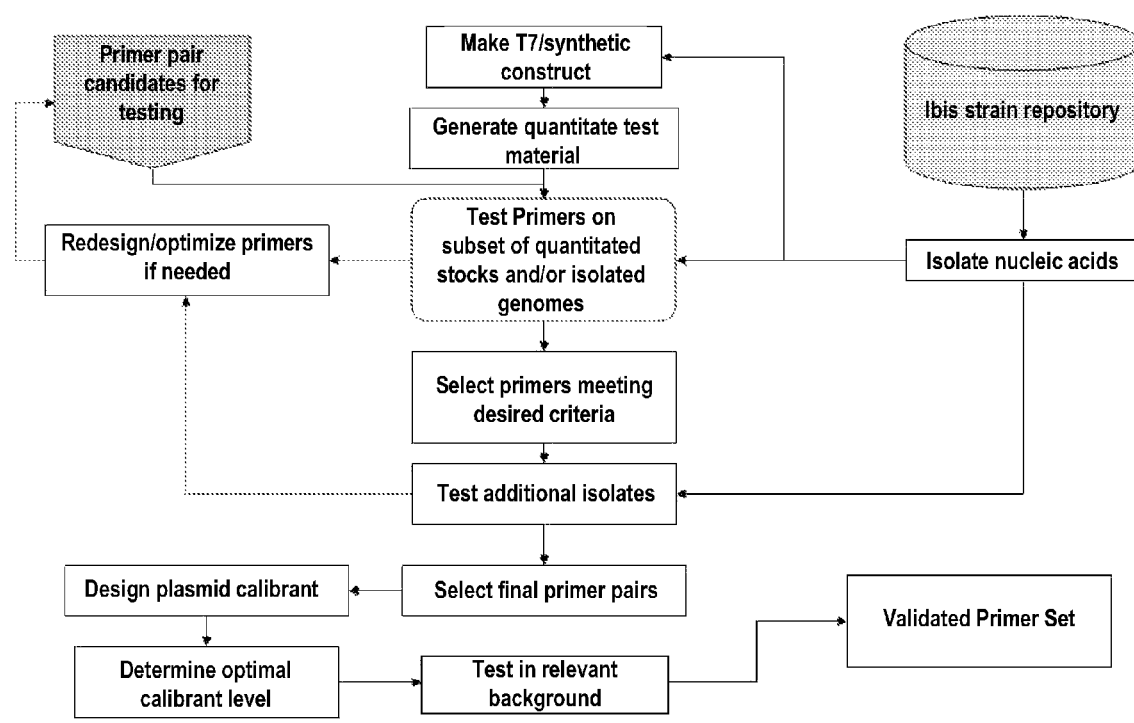
FIG. 5 shows a process diagram illustrating one embodiment of the primer pair validation process. Here select primers are shown meeting test criteria. Criteria include but are not limited to, the ability to amplify targeted bioagent nucleic acid, the ability to exclude non-target bioagents, the ability to not produce unexpected amplicons, the ability to not dimerize, the ability to have analytical limits of detection of ≤100 genomic copies/reaction, and the ability to differentiate amongst different target organisms.

One embodiment of a process flow diagram used for primer selection and validation process is depicted in FIGS. 4 and 5. For each group of organisms, candidate target sequences are identified (200) from which nucleotide sequence alignments are created (210) and analyzed (220). Primers are then configured by selecting priming regions (230) to facilitate the selection of candidate primer pairs (240). The primer pair sequence is typically a "best fit" amongst the aligned sequences, such that the primer pair sequence may or may not be fully complementary to the hybridization region on any one of the bioagents in the alignment. Thus, best fit primer pair sequences are those with sufficient complementarity with two or more bioagents to hybridize with the two or more bioagents and generate an amplicon. The primer pairs are then subjected to in silico analysis by electronic PCR (ePCR) (300) wherein bioagent identifying amplicons are obtained from sequence databases such as GenBank or other sequence collections (310) and tested for specificity in silico (320). Bioagent identifying amplicons obtained from ePCR of GenBank sequences (310) may also be analyzed by a probability model which predicts the capability of a given amplicon to identify unknown bioagents. Preferably, the base compositions of amplicons with favorable probability scores are then stored in a base composition database (325). Alternatively, base compositions of the bioagent identifying amplicons obtained from the primers and GenBank sequences are directly entered into the base composition database (330). Candidate primer pairs (240) are validated by in vitro amplification by a method such as PCR analysis (400) of nucleic acid from a collection of organisms (410). Amplicons thus obtained are analyzed to confirm the sensitivity, specificity and reproducibility of the primers used to obtain the amplicons (420).

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

The primers, in some embodiments, are employed as compositions for use in methods for identification of bioagents as follows: a primer pair composition is contacted with nucleic acid of an unknown isolate suspected of comprising a target bioagent. The nucleic acid is then amplified by a nucleic acid amplification technique, such as PCR for example, to obtain an amplicon that represents a bioagent identifying amplicon. The base composition of the double-stranded amplicon, or single strand corresponding to only the forward or reverse primer, is determined by techniques such as sequencing, HPLC, and paper chromatography (see, e.g., Voelkerding et al., *Clinical Chem.*, "Next-generation sequencing: from basic research to diagnostics," 55: 641-658, 2009; MacLean et al., *Nature Rev. Microbiol.,* 7: 287-296, and Manderville and Kropinski, "Approaches to the Compositional Analysis of DNA," Methods Mol Biol. 2009; 502:11-7, all of which are herein incorporated by reference). A measured base composition calculated therefrom is then compared with a database of base compositions indexed to primer pairs and to known bioagents. A match between the base composition of the amplicon and the database base composition for that indexed primer pair correlates the measured base composition with an indexed bioagent, thus identifying the unknown bioagent (e.g. the species of virus). In some embodiments, the method is repeated using a different primer pair to resolve possible ambiguities in the identification process or to improve the confidence level for the identification assignment (triangulation identification). In some embodiments, for example, where the unknown is a novel, previously uncharacterized organism, the base composition from an amplicon generated from the unknown is matched with one or more best match base compositions from a database to predict a family, genus, species, sub-type, etc. of the unknown. Such information may assist further characterization of the unknown or provide a physician treating a patient infected by the unknown with a therapeutic agent best calculated to treat the patient.

In certain embodiments, the bioagent is detected with the systems and methods of the present invention in combination with other bioagents, including viruses, bacteria, fungi, or other bioagents. In particular embodiments, a panel is employed that includes a first bioagent and other related or un-related bioagents. Such panels may be specific for a particular type of bioagent, or specific for a specific type of test (e.g., for testing the safety of blood, one may include commonly present viral pathogens such as HCV, HIV, and bacteria that can be contracted via a blood transfusion).

In some embodiments, a bioagent identifying amplicon may be produced using only a single primer (either the forward or reverse primer of any given primer pair), provided an appropriate amplification method is chosen, such as, for example, low stringency single primer PCR (LSSP-PCR).

In some embodiments, the oligonucleotide primers are broad range survey primers which hybridize to conserved regions of nucleic acid. The broad range primer may identify the unknown bioagent depending on which bioagent is in the sample. In other cases, the base composition of an amplicon does not provide sufficient resolution to identify the unknown bioagent as any one bioagent at or below the species level. These cases generally benefit from further analysis of one or more amplicons generated from at least one additional broad range survey primer pair, or from at least one additional division-wide primer pair, or from at least one additional drill-down primer pair. Identification of sub-species characteristics may be required, for example, to determine a clinical treatment of patient, or in rapidly responding to an outbreak of a new species, sub-type, etc. of pathogen to prevent an epidemic or pandemic.

One with ordinary skill in the art of design of amplification primers will recognize that a given primer need not hybridize with 100% complementarity in order to effectively prime the synthesis of a complementary nucleic acid strand in an amplification reaction. Primer pair sequences may be a "best fit" amongst the aligned bioagent sequences, thus they need not be fully complementary to the hybridization region of any one of the bioagents in the alignment. Moreover, a primer may hybridize over one or more segments such that intervening or adjacent segments are not involved in the hybridization event (e.g., for example, a loop structure or a hairpin structure). Thus, in some embodiments, an extent of variation of 70% to 100%, or any range falling within, of the sequence identity is possible relative to the specific primer sequences disclosed herein. To illustrate, determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer. Percent identity need not be a whole number, for example when a 28 consecutive nucleobase primer is completely identical to a 31 consecutive nucleobase primer (28/31=0.9032 or 90.3% identical).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.,* 1981, 2, 482-489). In some embodiments, complementarity of primers with respect to the conserved priming regions of viral nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range falling within) sequence identity with the primer sequences specifically disclosed herein.

In some embodiments, the oligonucleotide primers are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated A residues as a result of the non-specific enzyme activity of, e.g., Taq DNA polymerase (Magnuson et al., *Biotechniques,* 1996, 21, 700-709), an occurrence which may lead to ambiguous results arising from molecular mass analysis.

Primers may contain one or more universal bases. Because any variation (due to codon wobble in the third position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" base pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., *Nucleosides and Nucleotides,* 1995, 14, 1001-1003), the degenerate nucleotides dP or dK, an acyclic nucleoside analog containing 5-nitroindazole (Van Aerschot et al., *Nucleosides and Nucleotides.,* 1995, 14, 1053-1056) or the purine analog 1-(2-deoxy-beta-D-ribofuranosyl)-imidazole-4-carboxamide (Sala et al., *Nucl. Acids Res.,* 1996, 24, 3302-3306).

In some embodiments, to compensate for weaker binding by the wobble base, oligonucleotide primers are configured such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S. Pre-Grant Publication No. 2003-0170682; also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, non-template primer tags are used to increase the melting temperature ($T_m$) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a possible source of ambiguity in the determination of base composition of amplicons.

In some embodiments, assignment of previously unobserved base compositions (also known as "true unknown base compositions") to a given phylogeny can be accomplished via the use of pattern classifier model algorithms. Base compositions, like sequences, may vary slightly from strain to strain within species, for example. In some embodiments, the pattern classifier model is the mutational probability model. In other embodiments, the pattern classifier is the polytope model. A polytope model is the mutational probability model that incorporates both the restrictions among strains and position dependence of a given nucleobase within a triplet. In certain embodiments, a polytope pattern classifier is used to classify a test or unknown organism according to its amplicon base composition.

In some embodiments, it is possible to manage this diversity by building "base composition probability clouds" around the composition constraints for each species. A "pseudo four-dimensional plot" may be used to visualize the concept of base composition probability clouds. Optimal primer design typically involves an optimal choice of bioagent identifying amplicons and maximizes the separation between the base composition signatures of individual bio-agents. Areas where clouds overlap generally indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of an unknown bioagent whose assigned base composition has not been previously observed and/or indexed in a bioagent identifying amplicon base composition database due to evolutionary transitions in its nucleic acid sequence.

Provided herein is bioagent classifying information at a level sufficient to identify a given bioagent. Furthermore, the process of determining a previously unknown base composition for a given bioagent (for example, in a case where sequence information is unavailable) has utility by providing additional bioagent indexing information with which to populate base composition databases. The process of future bioagent identification is thus improved as additional base composition signature indexes become available in base composition databases.

In certain embodiments, a sample comprising an unknown bioagent is contacted with a primer pair which amplifies the nucleic acid from the bioagent, and a known quantity of a polynucleotide that comprises a calibration sequence. The amplification reaction then produces two amplicons: a bioagent identifying amplicon and a calibration amplicon. The bioagent identifying amplicon and the calibration amplicon are distinguishable by base composition while being amplified at essentially the same rate. Effecting differential base compositions can be accomplished by choosing as a calibration sequence, a representative bioagent identifying amplicon (from a specific species of bioagent) and performing, for example, a 2-8 nucleobase deletion or insertion within the variable region between the two priming sites, a calibration sequence with a different base composition due to base substitutions. The amplified sample containing the bioagent identifying amplicon and the calibration amplicon is then subjected to base composition analysis (e.g., sequencing, HPLC, paper chromatography, etc.) without determining the molecular mass of the sequences. The resulting base composition analysis of the nucleic acid of the bioagent and of the calibration sequence provides base composition data and abundance data for the nucleic acid of the bioagent and of the calibration sequence. The base composition data obtained for the nucleic acid of the bioagent enables identification of the unknown bioagent by base composition analysis. The abundance data enables calculation of the quantity of the bioagent, based on the knowledge of the quantity of calibration polynucleotide contacted with the sample.

In some embodiments, construction of a standard curve in which the amount of calibration or calibrant polynucleotide spiked into the sample is varied provides additional resolution and improved confidence for the determination of the quantity of bioagent in the sample. Alternatively, the calibration polynucleotide can be amplified in its own reaction vessel or vessels under the same conditions as the bioagent. A standard curve may be prepared there from, and the relative abundance of the bioagent determined by methods such as linear regression. In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single construct (preferably a vector) which functions as the calibration polynucleotide.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide gives rise to a calibration amplicon. Failure to produce a measurable calibration amplicon indicates a failure of amplification or subsequent analysis step such as amplicon purification or base composition determination. Reaching a conclusion that such failures have occurred is, in itself, a useful event. In some embodiments, the calibration sequence is comprised of DNA. In some embodiments, the calibration sequence is comprised of RNA.

In some embodiments, a calibration sequence is inserted into a vector which then functions as the calibration polynucleotide. In some embodiments, more than one calibration sequence is inserted into the vector that functions as the calibration polynucleotide. Such a calibration polynucleotide is herein termed a "combination calibration polynucleotide." It should be recognized that the calibration method should not be limited to the embodiments described herein. The calibration method can be applied for determination of the quantity of any bioagent identifying amplicon when an appropriate standard calibrant polynucleotide sequence is designed and used.

In certain embodiments, primer pairs are configured to produce bioagent identifying amplicons within more conserved regions of a bioagent, while others produce bioagent identifying amplicons within regions that are may evolve more quickly. Primer pairs that characterize amplicons in a conserved region with low probability that the region will evolve past the point of primer recognition are useful, e.g., as a broad range survey-type primer. Primer pairs that characterize an amplicon corresponding to an evolving genomic region are useful, e.g., for distinguishing emerging bioagent strain variants.

The primer pairs described herein provide reagents, e.g., for identifying diseases caused by emerging types of bioagents. Base composition analysis eliminates the need for prior knowledge of bioagent sequence to generate hybridization probes. Thus, in another embodiment, there is provided a method for determining the etiology of a particular stain when the process of identification of is carried out in a clinical setting, and even when a new strain is involved. This is possible because the methods may not be confounded by naturally occurring evolutionary variations.

Another embodiment provides a means of tracking the spread of any species or strain of particular bioagents when a plurality of samples obtained from different geographical locations are analyzed by methods described above in an epidemiological setting. For example, a plurality of samples from a plurality of different locations may be analyzed with primers which produce bioagent identifying amplicons, a subset of which identifies a specific strain. The corresponding locations of the members of the strain-containing subset indicate the spread of the specific strain to the corresponding locations.

Also provided are kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to twenty primer pairs, from one to ten primer pairs, from one to eight pairs, from one to five primer pairs, from one to three primer pairs, or from one to two primer pairs.

In some embodiments, the kit may also comprise a sufficient quantity of reverse transcriptase, a DNA polymerase, suitable nucleoside triphosphates (including any of those described above), a DNA ligase, and/or reaction buffer, or any combination thereof, for the amplification processes described above. The kit may also comprise reagents necessary for performing sequencing methods, or HPLC or paper chromatography (see, e.g., Voelkerding et al., *Clinical Chem.*, "Next-generation sequencing: from basic research to diagnostics," 55: 641-658, 2009; MacLean et al., *Nature Rev. Microbiol.;* 7: 287-296, and Manderville and Kropinski, "Approaches to the Compositional Analysis of DNA," Methods Mol Biol. 2009; 502:11-7, all of which are herein incorporated by reference).

A kit may further include instructions pertinent for the particular embodiment of the kit, such instructions describing the primer pairs and amplification conditions for operation of the method. In some embodiments, the kit further comprises instructions for analysis, interpretation and dissemination of data acquired by the kit. In other embodiments, instructions for the operation, analysis, interpretation and dissemination of the data of the kit are provided on computer readable media. A kit may also comprise amplification reaction containers such as microcentrifuge tubes, microtiter plates, and the like. A kit may also comprise reagents or other materials for isolating bioagent nucleic acid or bioagent identifying amplicons from amplification reactions, including, for example, detergents, solvents, or ion exchange resins which may be linked to magnetic beads. A kit may also comprise a table of measured or calculated base compositions of bioagents using the primer pairs of the kit.

The invention also provides systems that can be used to perform various assays relating to bioagent detection or identification. In certain embodiments, systems include sequencing devices (or HPLC equipment or paper chromatography equipment) configured to detect base compositions of amplicons produced using purified oligonucleotide primer pairs described herein. Other devices/equipment that are optionally adapted for use in the systems of the invention are described further below. In some embodiments, systems also include controllers operably connected to sequencing devices and/or other system components. In some of these embodiments, controllers are configured to correlate the base compositions of the amplicons with bioagents to effect detection or identification. As described herein, the base compositions generally correspond to the bioagent species identities. In certain embodiments, controllers include, or are operably connected to, databases of known base compositions of amplicons of known species of bioagents produced with the primer pairs described herein. Controllers are described further below.

In certain embodiments, the oligonucleotides are arrayed on solid supports, whereas in others, they are provided in one or more containers, e.g., for assays performed in solution. In certain embodiments, the systems also include at least one detector or detection component (e.g., a spectrometer) that is configured to detect detectable signals produced in the container or on the support. In addition, the systems also optionally include at least one thermal modulator (e.g., a thermal cycling device) operably connected to the containers or solid supports to modulate temperature in the containers or on the solid supports, and/or at least one fluid transfer component (e.g., an automated pipettor) that transfers fluid to and/or from the containers or solid supports, e.g., for performing one or more assays (e.g., nucleic acid amplification, real-time amplicon detection, etc.) in the containers or on the solid supports.

Examples of suitable thermocycling devices that are optionally utilized are available from many different commercial suppliers, including Mastercycler® devices (Eppendorf North America, Westbury, N.Y., U.S.A.), the COBAS®AMPLICOR Analyzer (Roche Molecular Systems, Inc., Pleasanton, Calif., U.S.A.), Mycycler and iCycler Thermal Cyclers (Bio-Rad Laboratories, Inc., Hercules, Calif., U.S.A.), and the SmartCycler System (Cepheid, Sunnyvale, Calif. U.S.A.), among many others. In other exemplary embodiments, sample preparation components, nucleic acid amplification components, and related fluid handling or material transfer components are integrated with the systems described herein, e.g., to fully automate a given nucleic acid amplification and analysis process. Instruments that can be adapted for this purpose include, for example, the m2000™ automated instrument system (Abbott Laboratories, Abbott Park, Ill., U.S.A.), the GeneXpert System (Cepheid, Sunnyvale, Calif. U.S.A.), and the COBAS® AmpliPrep® System (Roche Molecular Systems, Inc., Pleasanton, Calif., U.S.A.), and the like.

Detectors are typically structured to detect detectable signals produced, e.g., in or proximal to another component of the given assay system (e.g., in a container and/or on a solid support). Suitable signal detectors that are optionally utilized, or adapted for use, herein detect, e.g., fluorescence, phosphorescence, radioactivity, absorbance, refractive index, luminescence, or mass. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, or scanning detectors. Detectors are also described in, e.g., Skoog et al., Principles of Instrumental Analysis, $6^{th}$ Ed., Brooks Cole (2006), Curren, Analytical Instrumentation: Performance Characteristics and Quality, John Wiley & Sons, Inc. (2000), Sharma et al., Introduction to Fluorescence Spectroscopy, John Wiley & Sons, Inc. (1999), Valeur, Molecular Fluorescence: Principles and Applications, John Wiley & Sons, Inc. (2002), and Gore, Spectrophotometry and Spectrofluorimetry: A Practical Approach, $2^{nd}$ Ed., Oxford University Press (2000), which are each incorporated by reference.

As mentioned above, the systems of the invention also typically include controllers that are operably connected to one or more components (e.g., detectors, databases, thermal modulators, fluid transfer components, robotic material handling devices, and the like) of the given system to control operation of the components. More specifically, controllers are generally included either as separate or integral system components that are utilized, e.g., to receive data from detectors to effect and/or regulate temperature in the containers, or to effect and/or regulate fluid flow to or from selected containers. Controllers and/or other system components are optionally coupled to an appropriately programmed processor, computer, digital device, information appliance, or other logic device (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display or liquid crystal display), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a graphic user interface (GUI), or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming.

Figure 6:
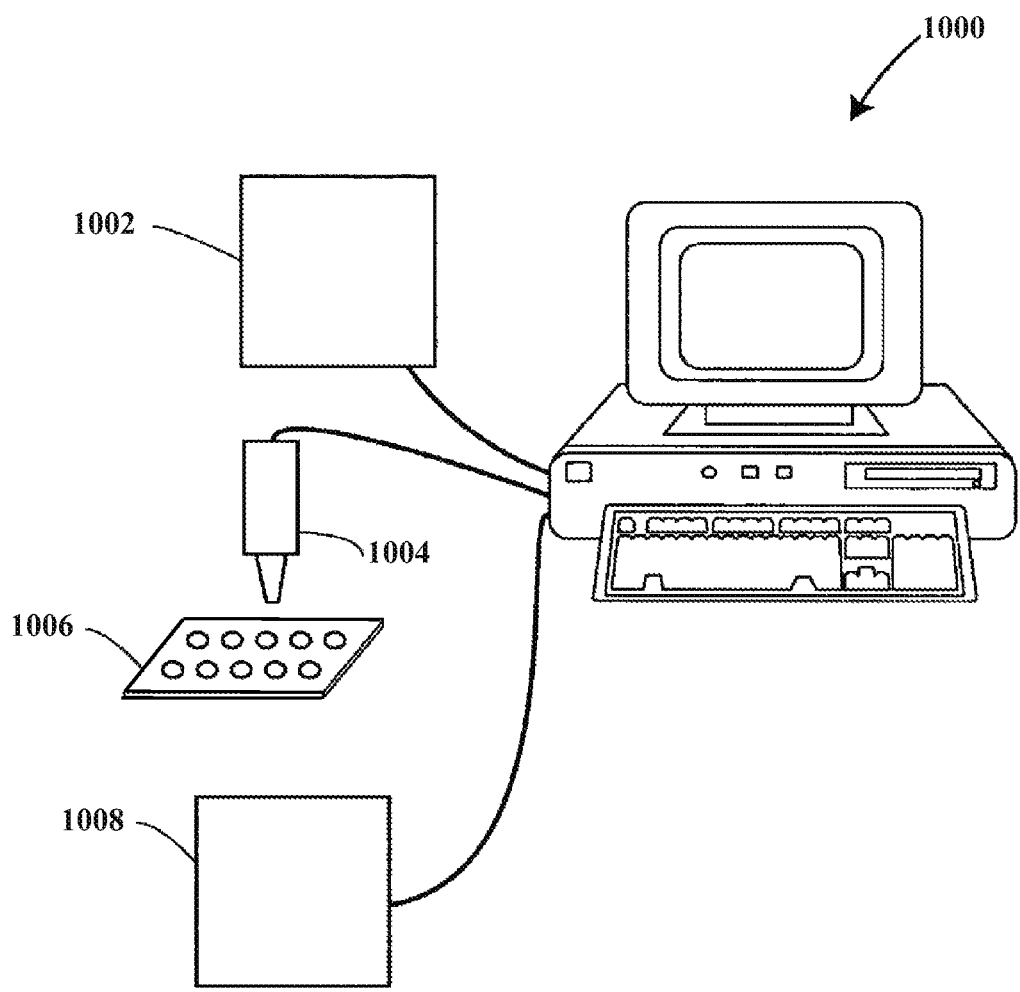
FIG. 6 shows a block diagram showing a representative system.

FIG. 6 is a schematic showing a representative system that includes a logic device in which various aspects of the present invention may be embodied. As will be understood by practitioners in the art from the teachings provided herein, aspects of the invention are optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform as desired. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

More specifically, FIG. 6 schematically illustrates computer 1000 to which sequencing device or system 1002 (e.g., SMRT detection array from Pacific Biosciences), fluid transfer component 1004 (e.g., a sample injection needle or the like), and database 1008 are operably connected. Optionally, one or more of these components are operably connected to computer 1000 via a server (not shown in FIG. 6). During operation, fluid transfer component 1004 typically transfers reaction mixtures or components thereof (e.g., aliquots comprising amplicons) from multi-well container 1006 to sequencing device. Sequencing device 1002 then detects the nucleic acid sequence of the amplicons. Computer 1000 then typically receives this sequence data, calculates base compositions from this data, and compares it with entries in database 1008 to identify species or strains of bioagents in a given sample. It will be apparent to one of skill in the art that one or more components of the system schematically depicted in FIG. 6 are optionally fabricated integral with one another (e.g., in the same housing).

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

Example 1

Non-Mass Determined Base Composition Analysis for Target Sequence Detection

This example illustrates that pathogens can be identified and distinguished from one another using complete or partial base composition or count information without the need for mass determination of bases. For example, Table I shows base composition (single strand) results for 16S_1100-1188 (16S rRNA) primer amplification reactions for different species of bacteria. Such base composition data can be generated by any type of sequencing methodology or system (see, e.g., Voelkerding et al., Clinical Chem., "Next-generation sequencing: from basic research to diagnostics," 55: 641-658, 2009; and MacLean et al., Nature Rev. Microbiol., 7: 287-296). Species which are repeated in the table (e.g., *Clostridium botulinum*) are different strains which have different base compositions in the 16S_1100-1188 region. As shown in Table I, for example, a complete base composition using this primer amplification reaction will uniquely identify and distinguish *Mycobacterium avium* (i.e., $A_{16}G_{32}C_{18}T_{16}$) from the other organisms listed in Table I, as will various partial base compositions using the same primer amplification reaction (e.g., $A_{16}G_{32}$, $A_{16}C_{18}T_{16}$, $G_{32}C_{18}T_{16}$, $C_{18}T_{16}$, etc.).

TABLE I

| Organism name | Base comp. |
|---|---|
| *Mycobacterium avium* | $A_{16}G_{32}C_{18}T_{16}$ |
| *Streptomyces* sp. | $A_{17}G_{38}C_{27}T_{14}$ |
| *Ureaplasma urealyticum* | $A_{18}G_{30}C_{17}T_{17}$ |
| *Streptomyces* sp. | $A_{19}G_{36}C_{24}T_{18}$ |
| *Mycobacterium leprae* | $A_{20}G_{32}C_{22}T_{16}$ |
| *M. tuberculosis* | $A_{20}G_{33}C_{21}T_{16}$ |
| *Nocardia asteroides* | $A_{20}G_{33}C_{21}T_{16}$ |
| *Fusobacterium necroforum* | $A_{21}G_{26}C_{22}T_{16}$ |
| *Listeria monocytogenes* | $A_{21}G_{27}C_{19}T_{19}$ |
| *Clostridium botulinum* | $A_{21}G_{27}C_{19}T_{21}$ |
| *Neisseria gonorrhoeae* | $A_{21}G_{28}C_{21}T_{18}$ |
| *Bartonella quintana* | $A_{21}G_{30}C_{22}T_{16}$ |
| *Enterococcus faecalis* | $A_{22}G_{27}C_{20}T_{19}$ |
| *Bacillus megaterium* | $A_{22}G_{28}C_{20}T_{18}$ |
| *Bacillus subtilis* | $A_{22}G_{28}C_{21}T_{17}$ |
| *Pseudomonas aeruginosa* | $A_{22}G_{29}C_{23}T_{15}$ |
| *Legionella pneumophila* | $A_{22}G_{32}C_{20}T_{16}$ |
| *Mycoplasma pneumoniae* | $A_{23}G_{20}C_{14}T_{16}$ |
| *Clostridium botulinum* | $A_{23}G_{26}C_{20}T_{19}$ |
| *Enterococcus faecium* | $A_{23}G_{26}C_{21}T_{18}$ |
| *Acinetobacter calcoaceti* | $A_{23}G_{26}C_{21}T_{19}$ |
| *Leptospira borgpeterseni* | $A_{23}G_{26}C_{24}T_{15}$ |
| *Leptospira interrogans* | $A_{23}G_{26}C_{24}T_{15}$ |
| *Clostridium perfringens* | $A_{23}G_{27}C_{19}T_{19}$ |
| *Bacillus anthracis* | $A_{23}G_{27}C_{20}T_{18}$ |
| *Bacillus cereus* | $A_{23}G_{27}C_{20}T_{18}$ |
| *Bacillus thuringensis* | $A_{23}G_{27}C_{20}T_{18}$ |
| *Aeromonas hydrophila* | $A_{23}G_{29}C_{21}T_{16}$ |
| *Escherichia coli* | $A_{23}G_{29}C_{21}T_{16}$ |
| *Pseudomonas putida* | $A_{23}G_{29}C_{21}T_{17}$ |
| *Escherichia coli* | $A_{23}G_{29}C_{22}T_{15}$ |
| *Shigella dysenteriae* | $A_{23}G_{29}C_{22}T_{15}$ |
| *Vibrio cholerae* | $A_{23}G_{30}C_{21}T_{16}$ |
| *Aeromonas hydrophila* | $A_{23}G_{31}C_{21}T_{15}$ |
| *Aeromonas salmonicida* | $A_{23}G_{31}C_{21}T_{15}$ |
| *Mycoplasma genitalium* | $A_{24}G_{19}C_{12}T_{18}$ |
| *Clostridium botulinum* | $A_{24}G_{25}C_{18}T_{20}$ |
| *Bordetella bronchiseptica* | $A_{24}G_{26}C_{19}T_{14}$ |
| *Francisella tularensis* | $A_{24}G_{26}C_{19}T_{19}$ |
| *Bacillus anthracis* | $A_{24}G_{26}C_{20}T_{18}$ |
| *Campylobacter jejuni* | $A_{24}G_{26}C_{20}T_{18}$ |
| *Staphylococcus aureus* | $A_{24}G_{26}C_{20}T_{18}$ |
| *Helicobacter pylori* | $A_{24}G_{26}C_{20}T_{19}$ |
| *Helicobacter pylori* | $A_{24}G_{26}C_{21}T_{18}$ |
| *Moraxella catarrhalis* | $A_{24}G_{26}C_{23}T_{16}$ |
| *Haemophilus influenzae* Rd | $A_{24}G_{28}C_{20}T_{17}$ |
| *Chlamydia trachomatis* | $A_{24}G_{28}C_{21}T_{16}$ |
| *Chlamydophila pneumoniae* | $A_{24}G_{28}C_{21}T_{16}$ |
| *C. pneumonia* Ar39 | $A_{24}G_{28}C_{21}T_{16}$ |
| *Pseudomonas putida* | $A_{24}G_{29}C_{21}T_{16}$ |
| *Proteus vulgaris* | $A_{24}G_{30}C_{21}T_{15}$ |
| *Yersinia pestis* | $A_{24}G_{30}C_{21}T_{15}$ |
| *Yersinia pseudotuberculosis* | $A_{24}G_{30}C_{21}T_{15}$ |
| *Clostridium botulinum* | $A_{25}G_{24}C_{18}T_{21}$ |
| *Clostridium tetani* | $A_{25}G_{25}C_{18}T_{20}$ |
| *Francisella tularensis* | $A_{25}G_{25}C_{19}T_{19}$ |
| *Acinetobacter calcoacetic* | $A_{25}G_{20}C_{20}T_{19}$ |
| *Bacteriodes fragilis* | $A_{25}G_{27}C_{16}T_{22}$ |
| *Chlamydophila psittaci* | $A_{25}G_{27}C_{21}T_{16}$ |
| *Borrelia burgdorferi* | $A_{25}G_{29}C_{17}T_{19}$ |
| *Streptobacillus monilifor* | $A_{26}G_{26}C_{20}T_{16}$ |
| *Rickettsia prowazekii* | $A_{26}G_{28}C_{18}T_{18}$ |
| *Rickettsia rickettsii* | $A_{26}G_{28}C_{20}T_{16}$ |
| *Mycoplasma mycoides* | $A_{28}G_{23}C_{16}T_{20}$ |

Some of these organisms can be distinguished using multiple primers. For example, *Chlamydia trachomatis* can be distinguished from *Chlamydia pneumoniae* AR39 and other organisms listed in Table II using the primer 16S_971-1062 and the primer 16S_1228-1310 in addition to 16S_1100-1188 based on a complete or partial base composition for the amplicons.

TABLE II

| Organism | 16S_971-1062 | 16S_1228-1310 | 16S_1100-1188 |
|---|---|---|---|
| *Aeromonas hydrophila* | $A_{21}G_{29}C_{22}T_{20}$ | $A_{22}G_{27}C_{21}T_{13}$ | $A_{23}G_{31}C_{21}T_{15}$ |
| *Aeromonas salmonicida* | $A_{21}G_{29}C_{22}T_{20}$ | $A_{22}G_{27}C_{21}T_{13}$ | $A_{23}G_{31}C_{21}T_{15}$ |
| *Bacillus anthracis* | $A_{21}G_{27}C_{22}T_{22}$ | $A_{24}G_{22}C_{19}T_{18}$ | $A_{23}G_{27}C_{20}T_{18}$ |
| *Bacillus cereus* | $A_{22}G_{27}C_{21}T_{22}$ | $A_{24}G_{22}C_{19}T_{18}$ | $A_{23}G_{27}C_{20}T_{18}$ |
| *Bacillus thuringiensis* | $A_{22}G_{27}C_{21}T_{22}$ | $A_{24}G_{22}C_{19}T_{18}$ | $A_{23}G_{27}C_{20}T_{18}$ |
| *Chlamydia trachomatis* | $A_{22}G_{26}C_{20}T_{23}$ | $A_{24}G_{23}C_{19}T_{16}$ | $A_{24}G_{28}C_{21}T_{16}$ |
| *Chlamydia pneumoniae* AR39 | $A_{26}G_{23}C_{20}T_{22}$ | $A_{26}G_{22}C_{16}T_{18}$ | $A_{24}G_{28}C_{21}T_{16}$ |
| *Leptospira borgpetersenii* | $A_{22}G_{26}C_{20}T_{21}$ | $A_{22}G_{25}C_{21}T_{15}$ | $A_{23}G_{26}C_{24}T_{15}$ |
| *Leptospira interrogans* | $A_{22}G_{26}C_{20}T_{21}$ | $A_{22}G_{25}C_{21}T_{15}$ | $A_{23}G_{26}C_{24}T_{15}$ |
| *Mycoplasma genitalium* | $A_{28}G_{23}C_{15}T_{22}$ | $A_{30}G_{18}C_{15}T_{19}$ | $A_{24}G_{19}C_{12}T_{18}$ |
| *Mycoplasma pneumoniae* | $A_{28}G_{23}C_{15}T_{22}$ | $A_{27}G_{19}C_{16}T_{20}$ | $A_{23}G_{20}C_{14}T_{16}$ |
| *Escherichia coli* | $A_{22}G_{28}C_{20}T_{22}$ | $A_{24}G_{25}C_{21}T_{13}$ | $A_{23}G_{29}C_{22}T_{15}$ |
| *Shigella dysenteriae* | $A_{22}G_{28}C_{21}T_{21}$ | $A_{24}G_{25}C_{21}T_{13}$ | $A_{23}G_{29}C_{22}T_{15}$ |
| *Proteus vulgaris* | $A_{23}G_{26}C_{22}T_{21}$ | $A_{26}G_{24}C_{19}T_{14}$ | $A_{24}G_{30}C_{21}T_{15}$ |
| *Yersinia pestis* | $A_{24}G_{25}C_{21}T_{22}$ | $A_{25}G_{24}C_{20}T_{14}$ | $A_{24}G_{30}C_{21}T_{15}$ |
| *Yersinia pseudotuberculosis* | $A_{24}G_{25}C_{21}T_{22}$ | $A_{25}G_{24}C_{20}T_{14}$ | $A_{24}G_{30}C_{21}T_{15}$ |
| *Francisella tularensis* | $A_{20}G_{25}C_{21}T_{23}$ | $A_{23}G_{26}C_{17}T_{17}$ | $A_{24}G_{26}C_{19}T_{19}$ |
| *Rickettsia prowazekii* | $A_{21}G_{26}C_{24}T_{25}$ | $A_{24}G_{23}C_{16}T_{19}$ | $A_{26}G_{28}C_{18}T_{18}$ |
| *Rickettsia rickettsii* | $A_{21}G_{26}C_{25}T_{24}$ | $A_{24}G_{24}C_{17}T_{17}$ | $A_{26}G_{28}C_{20}T_{16}$ |

Example 2

HPLC Base Composition Determination

Example 1 can be repeated and instead of sequencing methodologies, HPLC type methodologies can be used to determine base compositions of the various amplicons. Methods for determining base compositions with HPLC and UV-vis detection are described in Manderville and Kropinski, "Approaches to the Compositional Analysis of DNA," Methods Mol Biol. 2009; 502:11-7, which is herein incorporated by reference. Briefly, a given PCR primer-pair generated amplicon can be rendered single-stranded (e.g., by heat) and then the forward primer strand or reverse primer strand can be removed from the sample so only the sense strand or antisense strand is present. This can be done, for example, by subjecting the amplicon containing sample to a solid support that has the forward primer linked to the solid support. Sense strands can then hybridize to the solid support, while reverse strands are washed away. This purified sample can then digested (e.g., to completion) to generate monodeoxynucleosides (e.g., the sample can be expose to alkaline phosphatase and a phosphodiesterase, see Huang et al., Free Radical Biology & Medicine, 31:1341-1351, 2001, herein incorporated by reference). This sample may then be filtered to remove enzymes. This filtered sample is then injected onto a HPLC column (e.g., C18 column, such as 5 um Agilent ZORBAX Exlipse XDB C18 column, 4.6 mm×150 mm) with 0.1M triethylammonium acetate (pH 6.5) containing 5% CH3CN (buffer A) and 0.1M triethylammonium acetate (pH 6.5) containing 65% CH3CN (buffer B) operated at a flow rate of 1 ml/min and ambient temperature. This system may employ isocratic elution with 95% buffer A and 5% buffer B. The order of elution for these conditions is dC, dG, dT, dA. Standards for the four deoxynucleosides should be used for comparison and to generate standard curves that can be used for quantification. The amount of each deoxynucleoside in the single stranded amplicon is determined by integration to give the area under each peak in the HPLC trace. These areas must be divided by the following extinction coefficients at 254 nm to take into account the different absorptions of the deoxynucleosides at the detection wavelength (Connolly, 1991, "Oligonucleotides Containing Modified Bases, In F. Eckstein (Ed.), Oligonucleotides and Analogues A Practical Approach, Oxford University Press, New York, herein incorporated by reference). Levels of the normal nucleosides are quantified using the standard curves derived from standards. The extinction coefficients at 254 nm: dC ($6\times10^3$), dG ($13.5\times10^3$), T ($7\times10^3$), and dA ($14.3\times10^3$). Once the base compositions are determined in this manner, they can be compared to database entries and unknown bioagent amplicons can be identified.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, internet web sites, and the like) cited in the present application is incorporated herein by reference in its entirety.

I claim:

1. A method of classifying a bioagent template nucleic acid according to a subgenus or species, said method comprising:
    (a) amplifying a bioagent template nucleic acid in a sample using a primer pair to generate an amplicon,
    wherein said primer pair hybridizes to said bioagent template nucleic acid and said amplicon at regions conserved among a genus of bioagents, and
    wherein said conserved regions flank a variable region that differs between at least two or more species of said genus of bioagents;
    (b) determining a partial base count of at least a subsequence of said variable region using a method that does not measure molecular mass of said template nucleic acid by mass spectrometry, to produce partial base count data, wherein said partial base count data provides the number but not the linear order of only one, two, or three nucleobase types, and wherein said subsequence of said variable region is at least 17 nucleobases in length; and
    (c) querying a database in silico with said partial base count data,
    wherein said database comprises a collection of partial base composition entries that are each indexed to both: i) a particular subgenus or species, and ii) said primer pair used to generate said amplicon,
    wherein each of said partial base count entries provides the number but not the linear order of only one, two or three nucleobase types, and
    wherein said querying is performed by a computer processor coupled to a controller configured to query said database for a match of said partial base count data with at least one of said partial base count entries, thereby classifying said bioagent template nucleic acid according to said subgenus or said species.

2. The method of claim 1, wherein said template nucleic acid comprises DNA or RNA.

3. The method of claim 1, wherein said determining is performed in real-time.

4. The method of claim 1, wherein said template nucleic acid comprises a mammalian nucleic acid, a bacterial nucleic acid, a viral nucleic acid, a fungal nucleic acid, or a protozoal nucleic acid.

5. The method of claim 1, wherein said template nucleic acid is attached to a solid support.

6. The method of claim 1, wherein said subsequence of said variable region is at least 72 bases in length.

7. The method of claim 1, further comprising obtaining said template nucleic acid from one or more sample sources selected from the group consisting of: an environmental sample and a sample derived from a subject.

8. The method of claim 1, wherein (b) comprises contacting said variable region with at least one nucleotide incorporating biocatalyst, labeled nucleotides, and at least one primer nucleic acid that is at least partially complementary to at least a subsequence of said template nucleic acid, under conditions whereby said nucleotide incorporating biocatalyst extends said primer nucleic acid to produce an extended primer nucleic acid by incorporating said labeled nucleotides at a terminal end of said extended primer nucleic acid, wherein nucleotides that comprise different nucleobases comprise different labels, wherein said different labels produce detectable signals as or after said labeled nucleotides are incorporated at said terminal end of said extended primer nucleic acid, which detectable signals identify said labeled nucleotides incorporated at said terminal end of said extended primer nucleic acid and/or complementary nucleotides in said template nucleic acid, and wherein said detectable signals are detected as or after said labeled nucleotides are incorporated at said terminal end of said extended primer nucleic acid to thereby determine a partial base count of said subsequence of said template nucleic acid and/or the complement thereof.

9. The method of claim 8, wherein said labels comprise different fluorescent labels and wherein said detectable signals are detected using a fluorescence microscope.

10. The method of claim 8, wherein said terminal end of said extended primer nucleic acid is the 3' terminal end.

11. The method of claim 8, wherein said nucleotide incorporating biocatalyst comprises an enzyme selected from the group consisting of: a polymerase, a terminal transferase, a reverse transcriptase, a polynucleotide phosphorylase, and a telomerase.

12. The method of claim 8, nucleotide incorporating biocatalyst comprises one or more modifications.

13. The method of claim 8, wherein said nucleotide incorporating biocatalyst is an enzyme derived from an organism that is selected from the group consisting of: *Thermus antranikianii, Thermus aquaticus, Thermus caldophilus, Thermus chliarophilus, Thermus filiformis, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Anaerocellum thermophilum, Bacillus caldotenax*, and *Bacillus stearothermophilus*.

14. The method of claim 8, wherein said nucleotide incorporating biocatalyst comprises a Φ29 DNA polymerase.

15. The method of claim 8, wherein a label is attached to one of a heterocyclic base of a labeled nucleotide, a sugar moiety of a labeled nucleotide, and a phosphate group of a labeled nucleotide.

16. The method of claim 8, wherein a linker attaches a label to a labeled nucleotide.

17. The method of claim 8, wherein said extended primer nucleic acid is complementary to a subsequence of said template nucleic acid.

18. The method of claim 8, wherein said extended primer nucleic acid is complementary to a full-length sequence of said template nucleic acid.

19. The method of claim 8, wherein said label comprises a fluorescent dye, a non-fluorescent label, a colorimetric label, a chemiluminescent label, a bioluminescent label, a radioisotope, an antibody, an antigen, biotin, a hapten, or an enzyme.

20. The method of claim 19, wherein said label is a fluorescent dye selected from the group consisting of: a rhodamine dye, a fluorescein dye, a halofluorescein dye, a dichlororhodamine dye, an energy transfer dye, a Lucifer dye, Oregon Green, and a cyanine dye.

21. The method of claim 19, wherein said label is a fluorescent dye selected from the group consisting of: JOE, VIC, TET, HEX, PAM, R6G, R110, TAMRA, and ROX.

22. The method of claim 19, wherein said label is a radioisotope selected from the group consisting of: $^{3}$H, $^{14}$C, $^{22}$Na, $^{32}$P, $^{33}$P, $^{35}$S, $^{42}$K, $^{45}$Ca, $^{59}$Fe, $^{125}$I, and $^{203}$Hg.

23. A method of classifying a bioagent target nucleic acid in a sample according to a subspecies comprising:
   (a) amplifying a bioagent template nucleic acid in a sample using a primer pair to generate an amplicon,
   wherein said primer pair hybridizes to said bioagent template nucleic acid and said amplicon at regions conserved among a species of bioagents, and
   wherein said conserved regions flank a variable region that differs between at least two or more subspecies of said species of bioagents;
   (b) determining a partial base count of at least a subsequence of said variable region using a method that does not employ mass spectrometry to produce partial base count data, wherein said partial base count data provides the number, but not the linear order of, only one, two, or three nucleobase types, and wherein said subsequence of said variable region is at least 17 nucleobases in length; and
   (c) querying a database in silico with said partial base count data,
   wherein said database comprises a collection of partial base composition entries that are each indexed to both: i) a particular subspecies and ii) said primer pair used to generate said amplicon,
   wherein each of said partial base count entries provides the number but not the linear order of only one, two or three nucleobase types, and
   wherein said querying is performed by a computer processor coupled to a controller configured to query said database for a match of said partial base count data with at least one of said partial base count entries, thereby classifying said bioagent target nucleic acid according to said subspecies.

24. The method of claim 23, wherein said classifying said target nucleic acid is performed in real-time.

25. The method of claim 23, wherein said subsequence of said variable region is at least 72 bases in length.

26. The method of claim 1, wherein said partial base count entry provides the number but not linear order of A nucleobases and G nucleobases.

27. The method of claim 1, wherein said partial base count entry provides the number but not linear order of A nucleobases, C nucleobases and T nucleobases.

28. The method of claim 1, wherein said partial base count entry provides the number but not linear order of G nucleobases, C nucleobases and T nucleobases.

29. The method of claim 1, wherein said partial base count entry provides the number but not linear order of C nucleobases and T nucleobases.

* * * * *